US006720323B2

(12) United States Patent
Arnould

(10) Patent No.: US 6,720,323 B2
(45) Date of Patent: Apr. 13, 2004

(54) COLCHINOL DERIVATIVES AS ANGIOGENESIS INHIBITORS

(75) Inventor: Jean Claude Arnould, Reims (FR)

(73) Assignee: Angiogene Pharmaceuticals Limited, Oxford (GB)

( * ) Notice: Subject to any disclaimer, the term of this patent is extended or adjusted under 35 U.S.C. 154(b) by 0 days.

(21) Appl. No.: 10/332,271

(22) PCT Filed: Jul. 4, 2001

(86) PCT No.: PCT/GB01/02964
§ 371 (c)(1),
(2), (4) Date: Jan. 7, 2003

(87) PCT Pub. No.: WO02/08213
PCT Pub. Date: Jan. 31, 2002

(65) Prior Publication Data
US 2003/0195173 A1 Oct. 16, 2003

(51) Int. Cl.$^7$ .................. A61K 31/5375; A61P 35/00; C07D 295/14

(52) U.S. Cl. .................. 514/237.5; 544/154; 544/380; 548/338.1; 564/157; 558/172; 514/237.8

(58) Field of Search ................. 544/154, 380; 548/338.1; 564/157; 514/237.5

(56) References Cited

U.S. PATENT DOCUMENTS

| | | | |
|---|---|---|---|
| 3,442,953 | A | 5/1969 | Muller et al. |
| 5,561,122 | A | 10/1996 | Pettit |
| 5,760,092 | A | 6/1998 | Timashef et al. |
| 5,973,204 | A | 10/1999 | Bombardelli |
| 5,843,910 | A | 12/1999 | Bombardelli et al. |
| 6,080,739 | A | 6/2000 | Bombardelli |
| 6,423,753 | B1 | 7/2002 | Dougherty |

FOREIGN PATENT DOCUMENTS

| | | |
|---|---|---|
| FR | 4 685 M | 1/1967 |
| JP | 39-19634 | 9/1964 |
| JP | 39-19635 | 9/1964 |
| WO | 97/47577 | 12/1997 |
| WO | 99/02166 A | 1/1999 |
| WO | 99/02166 | 1/1999 |
| WO | 00/40529 | 7/2000 |
| WO | 00/48606 A1 | 8/2000 |
| WO | 02/04434 | 1/2002 |
| WO | 02/08213 | 1/2002 |

OTHER PUBLICATIONS

Abu Zarga et al., "New Natural Dibenzocycloheptylamine Alkaloids": A Possible Catabolic Route for the Colchicine Alkaloids", J. Nat. Prod., (1991), 54(4), 936–940.

Hunter et al., "The photo–oxidation of some novel Colchicine derivatives", Afinidad, vol. 38, No. 372, 1981, pp. 122–123.

Al–Tel et al., "New Natural Colchicinoids: Indications of Two Possible Catabolic Routes for the Colchicine Alkaloids", J. Nat. Prod., (1990) 53 (3), 623–629.

Banwell et al., "Total Synthesis of the Structures Assigned to Salimine and Jerusalemine, Alkaloids from *Colchicum decaisnei* Boiss. (Lilaceae)", J. Chem. Soc., Chem. Commun., (1994) (22) 2647–2649.

Banwell, et al., "Synthesis and Tubulin–Binding Properties of Some AC–and ABC–Ring Analogues of Allocolchicine", Aust J Chem., (1992), 45, 1967–1982.

Battersby et al., "Biosynthesis. Part 26$^1$. Synthetic Studies on Structural Modification of Late Biosynthetic Precursors for Colchicine", J. Chem. Soc., Perkin Trans 1, (1983), (12), 3053–3063.

Boger et al., "Thermal Reactions of Cyclopropenone Ketals. Application of . . . Total Synthesis of Colchicine", J. Am. Chem. Soc., (1986) (108 (21), 6713–6719.

Boyé et al. "185. Deaminocolchinyl Methyl Ether: Synthesis from . . . Errfects of Deaminocolchinyl Methyl Ether and Dehydro Analogs", Helv. Chem. Acta, (1989), 72 (8), 1690–1696.

Boyé et al. "Potential Covalent Markers of the Colchicine–Binding–Site . . . Isothiocyanato Groups", Med. Chem. Res., (1991), 1 (2), 142–150.

Boye et al., "Natural Products. Antitubulin effect of congeners of N–acetylocolchinyl . . . of demethoxy analogues of deaminocolchinyl methyl ether", Can. J. Chem., (1992), 70 (5), 1237–49.

(List continued on next page.)

*Primary Examiner*—Robert W. Ramsuer
(74) *Attorney, Agent, or Firm*—Morgan, Lewis & Bockius LLP

(57) ABSTRACT

The invention related to colchinol derivatives of the formula (I): Wherein: $R^1$, $R^2$ and $R^3$ are each independently hydroxy, phosphoryloxy (—$OPO_3H_2$), $C_{1-4}$alkoxy or an in vivo hydrolysable ester of hydroxy, with the proviso that at least 2 of $R^1$, $R^2$ and $R^3$ are $C_{1-4}$alkoxy; A is —CO—, —C(O)O—, —CON($R^8$)— (wherein $R^8$ is hydrogen, $C_{1-4}$alkyl, $C_{1-3}$alkoxy$C_{1-3}$alkyl, amino$C_{1-3}$alkyl or hydroxy$C_{1-3}$alkyl); a is an integer from 1 to 4 inclusive; $R^a$ and $R^b$ are independently selected from hydrogen, hydroxy and amino; B is —O—, —CO—, N($R^9$)CO—, —CON($R^9$)—, —N($R^9$)C(O)O—, —N($R^9$)CON($R^{10}$)—, —N($R^9$)SO$_2$—, —SO$_2$N($R^9$)— or a direct single blond (wherein $R^9$ and $R^{10}$ are independently selected from hydrogen, $C_{1-4}$alkyl, $C_{1-3}$alkoxy$C_{1-3}$alkyl, amino$C_{1-3}$alkyl and hydroxy$C_{1-3}$alkyl); b is 0 or an integer from 1 to 4 inclusive, (provided that when b is 0, B is a single direct bond); D is carboxy, sulpho, tetrazolyl, imidazolyl, phosphoryloxy, hydroxy, amino, N—($C_{1-4}$alkyl)amino, N,N-di($C_{1-3}$alkyl)amino, or of the formula —$Y^1(CH_2)_0R^{11}$ or —NHCH($R^{12}$)COOH; [wherein $Y^1$ is a direct single bond, —O—, —C(O)—, —N($R^{13}$)C(O)— or —C(O)N($R^{13}$)— (wherein $R^{13}$ is hydrogen, $C_{1-4}$alkyl, $C_{1-3}$alkoxy$C_{2-3}$alkyl, amino$C_{2-3}$alkyl or hydroxy$C_{2-3}$alkyl); e is 0 or an integer from 1 to 4 inclusive.

16 Claims, No Drawings

OTHER PUBLICATIONS

Boyé et al., "Synthesis of $^{14}$C Labelled Electrophilic Ligands of the Colchicine . . . 9–Deoxy–N–Acetylcolchinol.", J. Labelled Compd Radiopharm., (1993) 33(4), 293–299.

Brecht et al., "(−)–(M,7S)–Colchinine and (−)–(M, 7S)–10–Ethylthiocolchicide/Alkyne . . . Consecutive [4+2] and [3+2] Cycloadditions", Eur. Jour. Org. Chem., (1998) (11) 2451–2460.

Brossi et al., "aS, 7S–absolute configuration of natural (−)–colchinine and allcongeners", FEBS Lett., (1990), 262 (1), 5–7.

Deinum et al., "Synthesis and Binding to Tubulin of an Allocolchicine Spin Probe." Acta Chem. Scand, Ser B (1981) B35 (10), 677–81.

Dilger et al., "Arbeitsvorschriften und Meβwerte Procedures and Data Formaldehyd–O–oxid und Colchicine: ein eleganter Zugang zu Allocolcicinen", J. Prakt Chem./Chem–Ztg, (1998), 340 (5), 468–471 (in German).

Dokl Akad Nauk UzSSR, (1991) (4) 33–35.

Dumortier et al., "Alterations of Rings B and C of Colchicine Are Cumulative in Overall Binding to Tubulin but Modify Each Kinetic Step", Biochemistry, (1996), 35 (49), 15900–15906.

Fernholz, "Uber die Umlagerung des Colchicins mit Natriumalkoholat und die Stuktur des Ringes $C^1$)", Justus Liebigs Ann. Chem., CODEN: JLACBF, 568, (1950), 63–82.

Fitzgerald, "Molecular Features of Colchicine Associated with Antimitotic Activity and Inhibition of Tublin Polymerization", Biochemistry Pharmacology, (1976), 25, 1383–1387.

Ghera et al., "Total Synthesis of Lignan (±)–Schizandrin", J. Chem. Soc. Chem. Commun., (1978) (11), 480–481.

Hahn et al., "Synthesis and Evaluation of 2–Diazo–3,3, 3–Trifluoropropanoyl . . . Photochemistry, and Tubulin Binding", Photochem. Photobiol., (1992) 55 (1), 17–27.

Han et al., "Distances between the Paclitaxel, Colchicine, and Exchangeable GTP Binding Sites on Tubulin", Biochemistry, (1998), 37 (19), 6636–6644.

Hastie, "Spectroscopic analysis of colchicinoid–tubulin complexes", Cellular Pharmacology, (1993), 1 (Suppl. 1), S17–S21.

Hastie, "Spectroscopic and Kinetic Features of Allocolchicine Binding to Tubulin", Biochemistry, (1989), 28 (19), 7753–7760.

Hrbek et al., "Circular Dichroism of Alkaloids of Colchicine Type and Their Derivatives", Collect. Czech. Chem. Commun., (1982), 47 (8), 2258–79.

Iorio, "Contraction of the Tropolonic Ring of Colchicine by Hydrogen Peroxide Oxidation", Heterocycles, (1984), 22 (10), 2207–2211.

Izv Akad Nauk Turkm SSR, Ser Fiz–Tekh, Khim Geol Nauk, (1976), (1), 70–73.

Kiselev et al., "Benzenoid Rearrangement of Colchicine by the Action of Ethylene Glycol", Zh. Org. Khim., (1977), 13 (11), 2337–2342 (in Russian) (English translation attached).

Kislev et al., "Derivatives of Aminocolchicide VI" Obshch. Khim., (1970), 40 (4), 914–915 (in Russian, English translation attached).

Kiselev, "Derivatives of Aminocolchicide. VII", Zh. Zh. Obshch. Khim., (1971), 41 (2) 464–466 (in Russian, English translation attached).

Kita et al., "Non–phenolic oxidative coupling of phenol ether derivatives using phenyliodine (III) bis(trifluoroacetate)", Chem. Commun. (Cambridge), (1996) (12), 1481–1482.

Leiter et al., "Damage Induced in Sarcoma 37 with Chemical Agents III. Colchicine Derivatives Related to Trimethylcolchicinic Acid and to Colchinol", J. Natl. Cancer Inst., (1952), 13, 379–392.

Mackay et al., "Structures of Colchicine Analogues. IV. An Aminobromoallocolchicine, $C_{20}H_{22}Br_2N_2O_4$,", Acta Crystallogr, Section C: Cryst. Struct Commun, (1991) C47 (12), 2615–2618.

Medrano, "Roles of Colchicine Rings B and C in the Binding Process to Tubulin", Biochemistry, (1989), 28 (13), 5589–5599.

Menéndez et al., "A Thermodynamic Study of the Interaction of Tubulin with Colchinine Site Ligands", J. Biol. Chem., (1989), 264, (28), 16367–16371.

Olszewski et al., "Potential Photoaffinity Labels for Tubulin. Synthesis and . . . Colchicine, Combretastatin, and 3,4, 5–Trimethoxybiphenyl", J. Org. Chem., (1994), 59 (15) 4285–4296.

Ondra et al., "Colchicinoide–Ihre Toxizität Und Biologische Activität, Acta Univ Palacki Olomuc Fac Med, (1995) 139, 17–18.

Palmquist et al., "Anodic Oxidation of Phenolic Compounds. $4.^{1a}$ Scope and Mechanism of the Anodic Intramolecular Coupling of Phenolic Diarylalkanes", J. Am. Chem. Soc., (1976), 98(9), 2571–80.

Perez–Ramirez et al., "Cosolvent Modulation of the Tubulin–Colchicine GTPase–Activating Conformational Change: Strength of the Enzymatic Activity", Biochemistry, (1994), 33 (20), 6262–6267.

Timbekov et al., "Mass Spectrometric Study of Alkaloids of the Homoprophine, Homomorpine and Allocolchicine Series", "Tezisy Dokl.=Sov.–Indiiskii Simp. Khim. Prir. Soedin., 5th (1978), p. 85 (Chemical Abstracts attached).

Tojo et al., "The Dibenzocycloheptylamine Alkaloids", J. Nat. Prod., (1989), 52 (5), 1163–1166.

Ward et al., "Energy Transfer Studies of the Distance between the Colchicine Ruthenium Red, and BisANS Binding Sites on Calf Brain Tubulin", Biochemistry, (1994), 33, 11900–11908.

Ward et al., "Energy–Transfer Studies of the Distance . . . Binding Sites of Calf Brain Tubulin", Biochemistry, (1988), 27 (5), 1508–1514.

Wolff et al., "Cochicine Binding to Antibodies", J. Biol. Chem., (1980) 255 (15), 7144–7148.

Wosikowski et al., "Identification of Epidermal Growth Factor Receptor and c–erbB2 Pathway Inhibitors by Correlation With Gene Expression Patterns", J. Natl. Cancer Inst., (1997), 89 (20) 1505–1515.

Xie et al., "Synthesis of three new Schizandrin Analogues", Chin. Chem. Lett., (1998) 9 (7) 631–634.

Yusupov et al., "A Study of 2–Demethylallocolchicine and Its Derivatives", Khim. Prir. Soedin, (1973), (2), 194–196 (in Russian) (English Translation Attached).

Zh Obshch Khim., (1994) 64(5) 856–864 (in Russian).

Zweig et al., "Inhibition of Sodium Urate–Induced Rat Hindpaw Edema by Colchicine Derivatives: Correlation with Antimitotic Activity", J. Pharmacol. Exp. Therapeutics, (1972), 182(2), 344–350.

Zweig et al., "Interaction of Some Colchicine Analogs, Vinblastine and Podophyllotoxin with Rat Brain Microtubule Protein", Biochemistry Pharmacology, (1973), 22, 2141–2150.

U.S. patent application Ser. No. 09/869,925, Davis et al., filed Aug. 23, 2001.

U.S. patent application Ser. No. 09/477,805, Dougherty, filed Jan. 5, 2000, now U.S. Pat. No. 6,423,753.

U.S. patent application Ser. No. 10/332,129, Arnould et al., filed Jan. 6, 2003.

COLCHINOL DERIVATIVES AS ANGIOGENESIS INHIBITORS

The present invention relates to vascular damaging agents, to the use of compounds of the invention in the manufacture of medicaments for use in the production of antiangiogenic effects in warm-blooded animals such as humans, to processes for the preparation of such compounds, to pharmaceutical compositions containing such compounds as active ingredient, to methods for the treatment of disease states associated with angiogenesis and to the use of such compounds as medicaments.

Normal angiogenesis plays an important role in a variety of processes including embryonic development, wound healing and several components of female reproductive function. Undesirable or pathological angiogenesis has been associated with disease states including diabetic retinopathy, psoriasis, cancer, rheumatoid arthritis, atheroma, Kaposi's sarcoma and haemangioma (Fan et al, 1995, Trends Pharmacol. Sci. 16: 57–66; Folkman, 1995, Nature Medicine 1: 27–31). Formation of new vasculature by angiogenesis is a key pathological feature of several diseases (J. Folkman, New England Journal of Medicine 333, 1757–1763 (1995)). For example, for a solid tumour to grow it must develop its own blood supply upon which it depends critically for the provision of oxygen and nutrients; if this blood supply is mechanically shut off the tumour undergoes necrotic death. Neovascularisation is also a clinical feature of skin lesions in psoriasis, of the invasive pannus in the joints of rheumatoid arthritis patients and of atherosclerotic plaques. Retinal neovascularisation is pathological in macular degeneration and in diabetic retinopathy.

Reversal of neovascularisation by damaging the newly-formed vascular endothelium is expected to have a beneficial therapeutic effect. The present invention is based on the discovery of tricyclic compounds that surprisingly specifically damage newly formed vasculature without affecting the normal, established vascular endothelium of the host species, a property of value in the treatment of disease states associated with angiogenesis such as cancer, diabetes, psoriasis, rheumatoid arthritis, Kaposi's sarcoma, haemangioma, acute and chronic nephropathies, atheroma, arterial restenosis, autoimmune diseases, acute inflammation, endometriosis, dysfunctional uterine bleeding and ocular diseases with retinal vessel proliferation.

Compounds of the present invention are colchinol derivatives. Colchinol derivatives for example N-acetylcolchinol are known. Anti-tumour effects have been noted on animal models (see for example—Jnl. Natl. Cancer Inst. 1952, 13, 379–392). However, the effect studied was that of gross damage (haemorrhage, softening and necrosis) and there is no suggestion of treatment of inappropriate angiogenesis by destruction of neovasculature.

It is believed, though this is not limiting on the invention, that the use of compounds of the invention damages newly-formed vasculature, for example the vasculature of tumours, thus effectively reversing the process of angiogenesis as compared to known anti-angiogenic agents which tend to be less effective once the vasculature has formed.

According to one aspect of the present invention there is provided a compound of the formula (I):

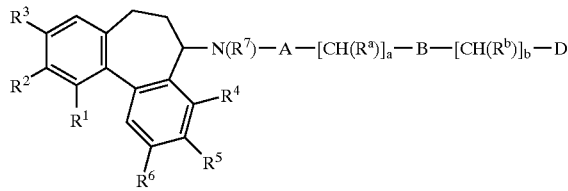

wherein:

$R^1$, $R^2$ and $R^3$ are each independently hydroxy, phosphoryloxy (—$OPO_3H_2$), $C_{1-4}$alkoxy or an in vivo hydrolysable ester of hydroxy, with the proviso that at least 2 of $R^1$, $R^2$ and $R^3$ are $C_{1-4}$alkoxy;

A is —CO—, —C(O)O—, —CON($R^8$)—, —$SO_2$— or —$SO_2$N($R^8$)— (wherein $R^8$ is hydrogen, $C_{1-4}$alkyl, $C_{1-3}$alkoxy$C_{1-3}$alkyl, amino$C_{1-3}$alkyl or hydroxy$C_{1-3}$alkyl);

a is an integer from 1 to 4 inclusive;

$R^a$ and $R^b$ are independently selected from hydrogen, hydroxy and amino;

B is —O—, —CO—, —N($R^9$)CO—, —CON($R^9$)—, —C(O)O—, —N($R^9$)—, —N($R^9$)C(O)O—, —N($R^9$)CON($R^{10}$)—, —N($R^9$)$SO_2$—, —$SO_2$N($R^9$)— or a direct single bond (wherein $R^9$ and $R^{10}$ are independently selected from hydrogen, $C_{1-4}$alkyl, $C_{1-3}$alkoxy$C_{1-3}$alkyl, amino$C_{1-3}$alkyl and hydroxy$C_{1-3}$alkyl);

b is 0 or an integer from 1 to 4 inclusive, (provided that when b is 0, B is a single direct bond);

D is carboxy, sulpho, tetrazolyl, imidazolyl, phosphoryloxy, hydroxy, amino, N—($C_{1-4}$alkyl)amino, N,N-di($C_{1-3}$alkyl)amino or of the formula —$Y^1$—$(CH_2)_cR^{11}$ or —NHCH($R^{12}$)COOH; [wherein $Y^1$ is a direct single bond, —O—, —C(O)—, —N($R^{13}$)—, —N($R^{13}$)C(O)— or —C(O)N($R^{13}$)— (wherein $R^{13}$ is hydrogen, $C_{1-4}$alkyl, $C_{1-3}$alkoxy$C_{2-3}$alkyl, amino$C_{2-3}$alkyl hydroxy$C_{2-3}$alkyl); c is 0 or an integer from 1 to 4 inclusive; $R^{11}$ is a 5-6-membered saturated heterocyclic group (linked via carbon or nitrogen) containing 1 or 2 ring heteroatoms, selected independently from O, S and N, or a 5-6-membered unsaturated or partially unsaturated heteroaryl group (linked via carbon or nitrogen) containing 1 or 2 ring heteroatoms, selected independently form O, S and N, which heterocyclic group or heteroaryl group may bear 1 or 2 substituents selected from:

oxo, hydroxy, halogeno, $C_{1-4}$alkyl, $C_{2-4}$alkanoyl, carbamoyl, N—($C_{1-4}$alkyl)carbamoyl, N,N-di-($C_{1-4}$alkyl)carbamoyl, hydroxy$C_{1-4}$alkyl, $C_{1-4}$alkoxy, cyano$C_{1-3}$alkyl, carbamoyl$C_{1-3}$alkyl, carboxy$C_{1-4}$alkyl, amino$C_{1-4}$alkyl, N—$C_{1-4}$alkylamino$C_{1-4}$alkyl, di-N,N—($C_{1-4}$alkyl)amino$C_{1-4}$alkyl, $C_{1-4}$alkoxy$C_{1-4}$alkyl, $C_{1-4}$alkylsulphonyl$C_{1-4}$alkyl and $R^{14}$ (wherein $R^{14}$ is a 5-6-membered saturated heterocyclic group (linked via carbon or nitrogen) containing 1 or 2 ring heteroatoms, selected independently from O, S and N, which heterocyclic group is optionally substituted by 1 or 2 substituents selected from:

oxo, hydroxy, halogeno, $C_{1-4}$alkyl, hydroxy$C_{1-4}$alkyl, $C_{1-4}$alkoxy, $C_{1-4}$alkoxy$C_{1-4}$alkyl and $C_{1-4}$alkylsulphonyl$C_{1-4}$alkyl);

$R^{12}$ is an amino acid side chain;

$R^5$ is $C_{1-4}$alkoxy;

$R^4$ and $R^6$ are each independently selected from: hydrogen, fluoro, nitro, amino, N—$C_{1-4}$alkylamino, N,N-di-($C_{1-4}$alkyl)amino, hydroxy, $C_{1-4}$alkoxy and $C_{1-4}$alkyl;

$R^7$ is hydrogen, $C_{1-4}$alkyl, $C_{1-3}$alkoxy$C_{1-3}$alkyl, amino $C_{1-3}$alkyl or hydroxy$C_{1-3}$alkyl; or a pharmaceutically-acceptable salt, solvate or pro-drug thereof.

In another aspect, the invention relates to a compound of the formula (I) as hereinabove defined or to a pharmaceutically-acceptable salt thereof.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

$R^{12}$ is an amino acid side chain. This includes side chains from natural and non-natural amino acids and includes the possibility of $R^{12}$ joining to the NH group so as to form a ring as in the amino acid proline. It includes α-amino acids β-amino acids and γ-amino acids. In addition, the amino acids may be L-isomers or D-isomers, but preferably L-isomers. Preferred amino acids include glycine, alanine, valine, leucine, isoleucine, methionine, proline, phenylalanine, tryptophan, serine, threonine, cysteine, tyrosine, asparaginine, glutamine, aspartic acid, glutamic acid, lysine, arginine, histidine, β-alanine and ornithine. More preferred amino acids include glutamic acid, serine, threonine, arginine, glycine, alanine, β-alanine and lysine. Especially preferred amino acids include glutamic acid, serine, threonine, arginine, alanine and β-alanine. Specific values for $R^{12}$ include hydrogen, $C_{1-4}$alkyl, $C_{1-4}$alkylthio $C_{1-4}$alkyl, hydroxy$C_{1-4}$alkyl, thio$C_{1-4}$alkyl, phenyl$C_{1-4}$alkyl (optionally substituted by hydroxy), guanidino$C_{1-4}$alkyl, carboxy$C_{1-4}$alkyl, carbamoyl$C_{1-4}$alkyl, amino$C_{1-4}$alkyl and imidazolyl $C_{1-4}$alkyl and $R^{12}$ forming a pyrrolidinyl ring with the NH group. Preferred values for $R^{12}$ include hydrogen, $C_{1-4}$alkyl, $C_{1-4}$alkylthio$C_{1-4}$alkyl, hydroxy$C_{1-4}$alkyl, thio$C_{1-4}$alkyl, guanidino$C_{1-4}$alkyl, carboxy$C_{1-4}$alkyl, carbamoyl$C_{1-4}$alkyl and amino$C_{1-4}$alkyl.

It is to be understood that, insofar as certain of the compounds of Formula (I) defined above may exist in optically active or racemic forms by virtue of one or more asymmetric carbon atoms, the invention includes in its definition any such optically active or racemic form which possesses vascular damaging activity. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques referred to hereinafter.

Suitable values for the generic radicals referred to above include those set out below. Within the present invention it is to be understood that a compound of the formula (I) or a salt thereof may exhibit the phenomenon of tautomerism and that the formulae drawings within this specification can represent only one of the possible tautomeric forms. It is to be understood that the invention encompasses any tautomeric form which has vascular damaging activity and is not to be limited merely to any one tautomeric form utilised within the formulae drawings.

It is also to be understood that certain compounds of the formula (I) and salts thereof can exist in solvated as well as unsolvated forms such as, for example, hydrated forms. It is to be understood that the invention encompasses all such solvated forms which have vascular damaging activity.

The present invention relates to the compounds of formula (I) as hereinbefore defined as well as to the salts thereof. Salts for use in pharmaceutical compositions will be pharmaceutically acceptable salts, but other salts may be useful in the production of the compounds of formula (I) and their pharmaceutically acceptable salts. Pharmaceutically acceptable salts of the invention may, for example, include acid addition salts of the compounds of formula (I) as hereinbefore defined which are sufficiently basic to form such salts. Such acid addition salts include for example salts with inorganic or organic acids affording pharmaceutically acceptable anions such as with hydrogen halides (especially hydrochloric or hydrobromic acid of which hydrochloric acid is particularly preferred) or with sulphuric or phosphoric acid, or with trifluoroacetic, citric or maleic acid. Suitable salts include hydrochlorides, hydrobromnides, phosphates, sulphates, hydrogen sulphates, alkylsulphonates, arylsulphonates, acetates, benzoates, citrates, maleates, fumarates, succinates, lactates and tartrates. In addition where the compounds of formula (I) are sufficiently acidic, pharmaceutically acceptable salts may be formed with an inorganic or organic base which affords a pharmaceutically acceptable cation. Such salts with inorganic or organic bases include for example an alkali metal salt, such as a sodium or potassium salt, an alkaline earth metal salt such as a calcium or magnesium salt, an ammonium salt or for example a salt with methylamine, dimethylamine, trimethylamine, piperidine, morpholine or tris-(2-hydroxyethyl)amine.

Various forms of prodrugs are known in the art. For examples of such prodrug derivatives, see:

a) Design of Prodrugs, edited by H. Bundgaard, (Elsevier, 1985) and Methods in Enzymology, Vol. 42, p. 309–396, edited by K. Widder, et al. (Academic Press, 1985);

b) A Textbook of Drug Design and Development, edited by Krogsgaard-Larsen and H. Bundgaard, Chapter 5 "Design and Application of Prodrugs", by H. Bundgaard p. 113–191 (1991);

c) H. Bundgaard, *Advanced Drug Deliveiy Reviews*, 8, 1–38 (1992);

d) H. Bundgaard, et al., *Journal of Pharmaceutical Sciences*, 77, 285 (1988); and e) N. Kakeya, et al., *Chem. Pharm. Bull.*, 32, 692 (1984).

Examples of such pro-drugs may be used to form in-vivo-cleavable esters of a compound of the Formula (I). An in-vivo-cleavable ester of a compound of the Formula (I) containing a carboxy group is, for example, a pharmaceutically-acceptable ester which is cleaved in the human or animal body to produce the parent acid. Suitable pharmaceutically-acceptable esters for carboxy include $C_{1-6}$alkoxymethyl esters, for example methoxymethyl; $C_{1-6}$alkanoyloxymethyl esters, for example pivaloyloxymethyl; phthalidyl esters; $C_{3-8}$cycloalkoxycarbonyloxy $C_{1-6}$alkyl esters, for example 1-cyclohexylcarbonyloxyethyl; 1,3-dioxolan-2-ylmethyl esters, for example 5-methyl-1,3-dioxolan-2-ylmethyl; and $C_{1-6}$alkoxycarbonyloxyethyl esters, for example 1-methoxycarbonyloxyethyl; and may be formed at any carboxy group in the compounds of this invention.

Suitable values for $R^1$, $R^2$, $R^3$ $R^4$, $R^5$, $R^6$, $R^7$, $R^8$, $R^9$, $R^{10}$ or $R^{13}$ or for various substituents on D or $R^{14}$ include:

| | |
|---|---|
| for halogeno | fluoro, chloro, bromo and iodo; |
| for $C_{1-4}$alkyl: | methyl, ethyl, propyl, isopropyl and tert-butyl; |
| for N-$C_{1-4}$alkylamino: | methylamino, ethylamino, propylamino, isopropylamino and butylamino; |
| for N,N-di-[$C_{1-4}$alkyl]amino: | dimethylamino, diethylamino, N-ethyl-N-methylamino and diisopropylamino; |
| for $C_{2-4}$alkanoyl: | acetyl and propionyl; |
| for $C_{1-4}$alkoxy: | methoxy and ethoxy; |
| for cyano$C_{1-4}$alkyl: | cyanomethyl and 2-cyanoethyl; |
| for N-$C_{1-4}$alkylcarbamoyl: | N-methylcarbamoyl, N-ethylcarbamoyl and N-propylcarbamoyl; |
| for N,N-di-[($C_{1-4}$))alkyl]carbamoyl: | N,N-dimethylcarbamoyl, N-ethyl-N-methylcarbamoyl and N,N-diethylcarbamoyl; |
| for $C_{1-4}$alkyl-sulphonylalkyl: | methylsulphonylmethyl and ethylsulphonylmethyl; |
| for hydroxy$C_{1-4}$alkyl: | hydroxymethyl, 2-hydroxyethyl, 1-hydroxyethyl and 3-hydroxypropyl as appropriate; |
| for $C_{1-4}$alkoxy$C_{1-4}$alkyl: | methoxymethyl, ethoxymethyl, 1-methoxyethyl, 2-methoxyethyl, 2-ethoxyethyl and 3-methoxypropyl as appropriate; |
| for amino$C_{1-4}$alkyl | aminomethyl, 2-aminoethyl, 1-aminoethyl and 3-aminopropyl as appropriate; |
| for N-$C_{1-4}$alkylamino$C_{1-4}$alkyl: | methylaminomethyl, ethylaminomethyl, 1-methylaminoethyl, 2-methylaminoethyl, 2-ethylaminoethyl and 3-methylaminopropyl as appropriate; |
| for N,N-di-[$C_{1-4}$alkyl]amino$C_{1-4}$alkyl: | dimethylaminomethyl, diethylaminomethyl, 1-dimethylaminoethyl, 2-dimethylaminoethyl and 3-dimethylaminopropyl as appropriate: |
| for carboxy$C_{1-4}$alkyl: | carboxymethyl, 1-carboxyethyl, 2-carboxyethyl, 3-carboxypropyl and 4-carboxybutyl; |
| for carbamoyl$C_{1-4}$alkyl: | carbamoylmethyl, 1-carbamoylethyl, 2-carbamoylethyl and 3-carbamoylpropyl; |
| for $C_{1-4}$alkoxy$C_{1-4}$alkyl | methoxymethyl, ethoxyethyl, methoxyethyl, and methoxypropyl. |

Carbamoyl refers to —$CONH_2$.

Piperazino refers to piperazin-1-yl.

Examples of 5- or 6-membered saturated heterocyclic groups include pyrrolidinyl, imidazolidinyl, pyrazolidinyl, piperidyl, piperazinyl and morpholinyl.

Examples of 5- or 6-membered unsaturated or partially unsaturated heteroaryl groups include: imidazolyl, imidazolinyl pyridyl pyrrolyl, furanyl, triazolyl, pyrazinyl, pyrazolinyl, pyrimidinyl, pyridazinyl, isoxazolyl, oxazolyl, isothiazolyl, thiazolyl and thienyl.

Preferably at least 2 of $R^1$, $R^2$, and $R^3$ are methoxy.

Preferably $R^1$, $R^2$, and $R^3$ are all $C_{1-4}$alkoxy.

Most preferably $R^1$, $R^2$, and $R^3$ are all methoxy.

Preferably $R^8$ is hydrogen, methyl, ethyl, 2-methoxyethyl, 2-aminoethyl or 2-hydroxyethyl.

More preferably $R^8$ is hydrogen, 2-aminoethyl or 2-hydroxyethyl and most preferably $R^8$ is hydrogen.

Preferably A is —CO—, —C(O)O— or —CON($R^8$)—. Most preferably A is —C(O)O—.

Preferably a is 1, 2 or 3 and most preferably a is 2 or 3.

Preferably $R^a$, and $R^b$ are hydrogen.

Preferably B is —N($R^9$)CO—, —CON($R^9$), —C(O)O—, —N($R^9$)—, —N($R^9$)C(O)O—, N($R^9$)CON($R^{10}$)— or a single direct bond.

More preferably B is —CO—, —N($R^9$)CO— or a single direct bond.

Yet more preferably B is —CO— or a single direct bond.

Most preferably B is —CO—. In another aspect B is a single direct bond.

Preferably $R^9$, and $R^{10}$ are independently selected from hydrogen, methyl, ethyl, 2-methoxyethyl, 2-aminoethyl and 2-hydroxyethyl.

More preferably $R^9$ and $R^{10}$ are independently selected from hydrogen, 2-aminoethyl and 2-hydroxyethyl.

Most preferably $R^9$ and $R^{10}$ are hydrogen.

Preferably b is 0, 1 or 2, more preferably b is 0 or 1 and most preferably b is 0.

Preferably $R^{11}$ is a 5 or 6 membered saturated heterocyclic ring containing 1 or 2 ring heteroatoms selected from N and O.

More preferably $R^{11}$ is a 6 membered saturated heterocyclic ring containing 1 or 2 ring heteroatoms selected from N and O.

Further preferably $R^{11}$ contains at least 1 ring nitrogen atom.

Further preferably $R^{11}$ is piperazinyl, morpholinyl or piperidinyl, each of which is linked via a ring carbon or nitrogen ring atom and each ring is optionally substituted by 1 or 2 of the substituents mentioned above for $R^{11}$.

Further preferably $R^{11}$ is linked via a ring nitrogen atom.

Most preferably $R^{11}$ is piperazino or morpholino, each ring being optionally substituted by 1 or 2 of the substituents mentioned hereinabove for $R^{11}$.

The saturated heterocyclic ring may be substituted on ring carbon or ring nitrogen atoms, providing this does not result in quaternisation.

Preferred substituents for the saturated heterocyclic ring in $R^{11}$ include $C_{1-4}$ alkyl, $C_{2-4}$alkanoyl, carbamoyl, cyano$C_{1-3}$alkyl, hydroxy$C_{1-3}$alkyl, carboxy$C_{1-3}$alkyl and amino$C_{1-3}$alkyl.

More preferred substituents for the saturated heterocyclic ring in $R^{11}$ include $C_{1-3}$alkyl, $C_{2-3}$alkanoyl, carbamoyl and hydroxy$C_{2-3}$alkyl.

Yet more preferred substituents for the saturated heterocyclic ring in $R^{11}$ include methyl, acetyl, carbamoyl and 2-hydroxyethyl.

The most preferred substituents for the saturated heterocyclic ring include methyl, acetyl and carbamoyl.

Preferably the saturated heterocyclic ring in $R^{11}$ is unsubstituted or substituted by 1 substituent.

When the saturated heterocyclic ring in $R^{11}$ is morpholino, preferably it is unsubstituted. When the saturated heterocyclic ring in $R^{11}$ is piperazino, preferably it is unsubstituted or substituted by 1 substituent on a ring nitrogen atom.

Preferably $Y^1$ is —CONH— or —NHCO—.

Preferably c is 0, 1 or 2.

More preferably c is 0.

Preferred values for $R^{11}$ include morpholino, 4-methylpiperazin-1-yl and 4-acetylpiperazin-1-yl.

Preferably $R^{14}$ is morpholino or piperazin-I-yl, each optionally substituted by 1 or 2 substituents selected from $C_{1-3}$alkyl, hydroxy$C_{2-3}$alkyl, $C_{1-3}$alkoxy and $C_{1-3}$alkoxy $C_{1-3}$alkyl.

More preferably $R^{14}$ is morpholino, or piperazin-1-yl unsubstituted or substituted by methyl.

Preferably D is carboxy, phosphoryloxy, hydroxy, amino, N—$C_{1-4}$alkylamino, N,N-di($C_{1-4}$ alkyl)amino or of the formula —$Y^1(CH_2)_cR^{11}$ wherein $Y^1$, c and $R^{11}$ are as hereinabove defined.

More preferably D is carboxy phosphoryloxy, hydroxy, amino or of the formula —$Y^1$—$(CH_2)_cR^{11}$ wherein $Y^1$, c and $R^{11}$ are as hereinabove defined.

More preferably D is phosphoryloxy, amino or of the formula —$Y^1$—$(CH_2)_cR^{11}$ wherein $Y^1$, c and $R^{11}$ are as hereinabove defined.

Yet more preferably D is phosphoyloxy, amino or of the formula —$Y^1$—$(CH_2)_cR^{11}$ wherein $Y^1$ and c are as hereinabove defined and $R^{11}$ is morpholino, imidazolyl, or piperazinyl, which heterocyclic group may bear one or more substituents as defined above.

Yet more preferably D is phosphoyloxy, amino or of the formula —Y$^1$—(CH$_2$)$_c$R$^{11}$ wherein Y$^1$ and c are as hereinabove defined and R$^{11}$ is morpholino, imidazolyl, 4-methylpiperazin-1-yl or 4-acetylpiperazin-1-yl.

Yet even more preferably D is phosphoyloxy, amino or of the formula —Y$^1$—(CH$_2$)$_c$R$^{11}$ wherein Y$^1$ is a direct single bond and c is 0 and R$^{11}$ is morpholino, imidazol-1-yl; 4-methylpiperazin-1-yl or 4-acetylpiperazin-1-yl.

Preferably R$^5$ is methoxy.

Preferably R$^4$ and R$^6$ are independently selected from hydrogen, hydroxy, C$_{1-3}$ alkoxy, and C$_{1-3}$alkyl.

More preferably at least one of R$^4$ and R$^6$ is hydrogen. Most preferably R$^4$ and R$^6$ are both hydrogen.

Preferably R$^7$ is hydrogen or methyl. Most preferably R$^7$ is hydrogen.

A preferred class of compound is of the formula (I) wherein:

R$^1$, R$^2$, and R$^3$ are all C$_{1-4}$alkoxy;

R$^4$ and R$^6$ are independently selected from hydrogen, hydroxy, C$_{1-3}$ alkoxy, and C$_{1-3}$alkyl;

R$^5$ is methoxy;

A is —CO—, —C(O)O— or —CONH—;

a is 1, 2 or 3;

B is —CO—, —NHCO—, —CONH, —C(O)O—, —NH—, —NHC(O)O—, NHCONH— or a single direct bond;

b is 0, 1 or 2;

D is carboxy, sulpho, phosphoryloxy, hydroxy, amino, N—C$_{1-4}$ alkylamino, N,N-di(C$_{1-4}$ alkyl)amino or of the formula —Y$^1$(CH$_2$)$_c$R$^{11}$ (wherein Y$^1$ is —NHC(O)— or —C(O)NH—; c is 1 or 2; R$^{11}$ is a 5-6-membered saturated heterocyclic group (linked via nitrogen) containing 1 or 2 ring heteroatoms, selected independently from O and N, which heterocyclic group may bear 1 or 2 substituents selected from:

C$_{1-4}$ alkyl, C$_{2-4}$alkanoyl, carbamoyl, cyanoC$_{1-3}$alkyl, hydroxyC$_{1-3}$alkyl, carboxyC$_{1-3}$alkyl and aminoC$_{1-3}$ alkyl);

R$^7$ is hydrogen;

or a pharmaceutically-acceptable salt, solvate or pro-drug thereof.

Another preferred class of compound is of the formula (I) wherein:

R$^1$, R$^2$, and R$^3$ are all methoxy;

R$^4$ and R$^6$ are independently selected from hydrogen, hydroxy, methoxy and methyl;

R$^5$ is methoxy;

A is —CO—, —C(O)O— or —CONH—;

a is 2 or 3;

B is —CO—, —NHCO—, —CONH or a single direct bond;

b is 0 or 1;

D is carboxy, phosphoryloxy, hydroxy, amino, N—C$_{1-4}$ alkylamino, N,N-di(C$_{1-4}$ alkyl)amino or of the formula —Y$^1$(CH$_2$)$_c$R$^{11}$ (wherein Y$^1$ is —NHC(O)— or —C(O)NH—; c is 1 or 2; R$^{11}$ is piperazinyl, morpholinyl or piperidinyl, each of which is linked via a ring nitrogen atom and each ring is optionally substituted by 1 or 2 substituents selected from:

C$_{1-4}$alkyl, C$_{2-4}$alkanoyl, carbamoyl, cyanoC$_{1-3}$alkyl, hydroxyC$_{1-3}$alkyl, carboxyC$_{1-3}$alkyl and aminoC$_{1-3}$ alkyl);

R$^7$ is hydrogen;

or a pharmaceutically-acceptable salt, solvate or pro-drug thereof.

Another preferred class of compounds is that of the formula (II):

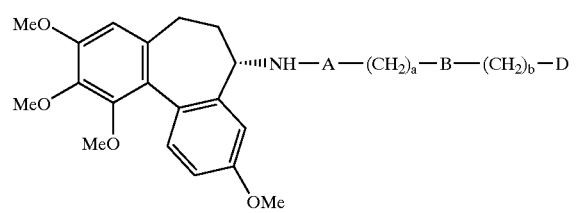

(II)

wherein a, b, A, B and D are as hereinabove defined;

or a pharmaceutically acceptable salt, solvate or prodrug thereof.

Another preferred class of compounds is that of the formula (II) wherein:

A is —CO—, —C(O)O— or —CONH—;

a is 2 or 3;

B is —CO—, —NHCO—, —CONH or a single direct bond;

b is 0 or 1;

D is carboxy, phosphoryloxy, hydroxy, amino, N—C$_{1-4}$ alkylamino, N,N-di(C$_{1-4}$ alkyl)amino or of the formula —Y$^1$(CH$_2$)$_c$R$^{11}$ (wherein Y$^1$ is —NHC(O)— or —C(O)NH—; c is 1 or 2; R$^{11}$ is piperazinyl, morpholinyl or piperidinyl, each of which is linked via a ring nitrogen atom and each ring is optionally substituted by 1 or 2 substituents selected from:

C$_{1-4}$alkyl, C$_{2-4}$alkanoyl, carbamoyl, cyanoC$_{1-3}$alkyl, hydroxyC$_{1-3}$alkyl, carboxyC$_{1-3}$alkyl and aminoC$_{1-3}$ alkyl);

or a pharmaceutically acceptable salt, solvate or prodrug thereof.

Another preferred class of compounds is that of the formula (II) wherein:

A is —CO—, —C(O)O— or —CONH—;

a is 2 or 3;

B is —CO—, —NHCO—, —CONH or a single direct bond;

b is 0 or 1;

D is phosphoryloxy, carboxy, amino or imidazolyl;

or a pharmaceutically acceptable salt, solvate or prodrug thereof.

Another preferred class of compounds is that of the formula (II) wherein:

A is —CO—, —C(O)O— or —CONH—;

a is 2 or 3;

B is —CO—, —NHCO— or a single direct bond;

b is 0 or 1;

D is phosphoryloxy amino or imidazolyl;

or a pharmaceutically acceptable salt, solvate or prodrug thereof.

A further preferred class of compounds of the invention is that of a compound of formula (III):

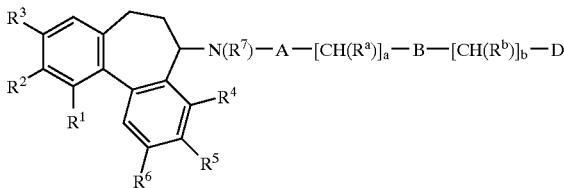

(III)

wherein:

$R^1$, $R^2$ and $R^3$ are each independently hydroxy, phosphoryloxy (—OPO$_3$H$_2$), C$_{1-4}$alkoxy or an in vivo hydrolysable ester of hydroxy, with the proviso that at least 2 of $R^1$, $R^2$ and $R^3$ are C$_{1-4}$alkoxy;

A is —CO—, —C(O)O—, —CON($R^8$)—, —SO$_2$— or —SO$_2$N($R^8$)— (wherein $R^8$ is hydrogen, C$_{1-4}$alkyl, C$_{1-3}$alkoxyC$_{2-3}$alkyl, aminoC$_{2-3}$alkyl or hydroxyC$_{2-3}$alkyl);

a is an integer from 1 to 4 inclusive;

$R^a$ and $R^b$ are independently selected from hydrogen, hydroxy and amino;

B is —O—, —CO—, —N($R^9$)CO—, —CON($R^9$)—, —C(O)O—, —N($R^9$)—, —N($R^9$)C(O)O—, —N($R^9$)CON($R^{10}$)—, —N($R^9$)SO$_2$—, —SO$_2$N($R^9$)— or a direct single bond (wherein $R^9$ and $R^{10}$ are independently selected from hydrogen, C$_{1-4}$alkyl, C$_{1-3}$alkoxyC$_{2-3}$alkyl, aminoC$_{2-3}$alkyl and hydroxyC$_{2-3}$alkyl);

b is 0 or an integer from 1 to 4 inclusive;

D is a 5-6-membered saturated heterocyclic group (linked via carbon or nitrogen) containing 1 or 2 ring heteroatoms, selected independently from O and N, which heterocyclic group may bear 1 or 2 substituents selected from:

oxo, hydroxy, halogeno, C$_{1-4}$alkyl, C$_{2-4}$alkanoyl, carbamoyl, N—(C$_{1-4}$alkyl)carbamoyl, N,N-di-(C$_{1-4}$alkyl)carbamoyl, hydroxyC$_{1-4}$alkyl, C$_{1-4}$alkoxy, cyanoC$_{1-3}$alkyl, carbamoylC$_{1-3}$alkyl, carboxyC$_{1-4}$alkyl, aminoC$_{1-4}$alkyl, N—C$_{1-4}$alkylaminoC$_{1-4}$alkyl, di-N,N—(C$_{1-4}$alkyl)aminoC$_{1-4}$alkyl, C$_{1-4}$alkoxyC$_{1-4}$alkyl, C$_{1-4}$alkylsulphonylC$_{1-4}$alkyl and $R^{14}$ (wherein $R^{14}$ is a 5-6-membered saturated heterocyclic group (linked via carbon or nitrogen) containing 1 or 2 ring heteroatoms, selected independently from O and N, which heterocyclic group is optionally substituted by 1 or 2 substituents selected from:

oxo, hydroxy, halogeno, C$_{1-4}$alkyl, hydroxyC$_{1-4}$alkyl, C$_{1-4}$alkoxy, C$_{1-4}$alkoxyC$_{1-4}$alkyl and C$_{1-4}$alkylsulphonylC$_{1-4}$alkyl);

$R^5$ is C$_{1-4}$alkoxy;

$R^4$ and $R^6$ are each independently selected from:
hydrogen, halogeno, nitro, amino, N—C$_{1-4}$alkylamino, N,N-di-(C$_{1-4}$alkyl)amino, hydroxy, C$_{1-4}$alkoxy and C$_{1-4}$alkyl;

$R^7$ is hydrogen, C$_{1-4}$alkyl, C$_{1-3}$alkoxyC$_{1-3}$alkyl, amino C$_{1-3}$alkyl or hydroxyC$_{1-3}$alkyl;

or a pharmaceutically acceptable salt, solvate or pro-drug thereof.

Another further preferred class of compound is of the formula (III) wherein:

$R^1$, $R^2$, and $R^3$ are all C$_{1-4}$alkoxy;

$R^4$ and $R^6$ are independently selected from hydrogen, hydroxy, C$_{1-3}$ alkoxy, and C$_{1-3}$alkyl;

$R^5$ is methoxy;

A is —CO—, —C(O)O— or —CONH—;

a is 1, 2 or 3;

B is —CO—, —NHCO—, —CONH, —C(O)O—, —NH—, —NHC(O)O—, NHCONH— or a single direct bond;

b is 0, 1 or 2;

D is piperazinyl or morpholinyl or piperidinyl, each ring being optionally substituted by 1 or 2 substituents selected from C$_{1-4}$alkyl, C$_{2-4}$alkanoyl, carbamoyl, cyanoC$_{1-3}$alkyl, hydroxyC$_{1-3}$alkyl, carboxyC$_{1-3}$alkyl and aminoC$_{1-3}$alkyl;

$R^7$ is hydrogen;

or a pharmaceutically-acceptable salt, solvate or pro-drug thereof.

Another further preferred class of compound is of the formula (III) wherein:

$R^1$, $R^2$, and $R^3$ are all methoxy;

$R^4$ and $R^6$ are independently selected from hydrogen, hydroxy, methoxy and methyl;

$R^5$ is methoxy;

A is —CO—, —C(O)O— or —CONH—;

a is 2 or 3;

B is —CO—, —NHCO—, —CONH or a single direct bond;

b is 0 or 1;

D is piperazino or morpholino, each ring being optionally substituted by 1 or 2 substituents selected from methyl, ethyl, acetyl, propionyl, carbamoyl and 2-hydroxyethyl;

$R^7$ is hydrogen;

or a pharmaceutically-acceptable salt, solvate or pro-drug thereof.

In another aspect the invention relates to a compound of the formula (IV):

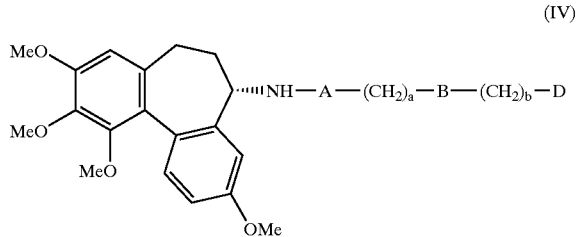

(IV)

wherein a, b, A, B and D are as hereinabove defined for formula (III);

or a pharmaceutically-acceptable salt, solvate or pro-drug thereof.

Another preferred class of compounds is that of the formula (IV) wherein:

A is —CO—, —C(O)O— or —CONH—;

a is 2 or 3;

B is —CO—, —NHCO—, —CONH or a single direct bond;

b is 0 or 1;

D is piperazino or morpholino, each ring being optionally substituted by 1 or 2 substituents selected from methyl, ethyl, acetyl, propionyl, carbamoyl and 2-hydroxyethyl;

or a pharmaceutically acceptable salt, solvate or pro-drug thereof.

Another preferred class of compounds is that of the formula (IV) wherein:

A is —CO—, —C(O)O— or —CONH—;
a is 2 or 3;
B is —CO—, —NHCO—, —CONH or a single direct bond;
b is 0 or 1;
D is morpholino, 4-methylpiperazin-1-yl or 4-acetylpiperazin-1-yl;

or a pharmaceutically acceptable salt, solvate or pro-drug thereof.

Another preferred class of compounds is that of the formula (IV) wherein:

A is —CO—, —C(O)O— or —CONH—;
a is 2 or 3;
B is —CO— or a single direct bond;
b is 0;
D is morpholino, 4-methylpiperazin-1-yl or 4-acetylpiperazin-1-yl;

or a pharmaceutically acceptable salt, solvate or pro-drug thereof.

Particular compounds of the present invention include:

N-[(5S)-3,9,10,11-tetramethoxy-6,7-dihydro-5H-dibenzo[a,c]cyclohepten-5-yl]-2-[2-aminoacetylamino]acetamide;

4-oxo4-[(5S)-3,9,10,11-tetramethoxy-6,7-dihydro-5H-dibenzo[a,c]cyclohepten-5-yl]amino]butyl disodium phosphate;

N-{N-[2-(imidazol-1-yl)ethyl]carbamoyl}-5(S)-3,9,10,11-tetramethoxy-6,7-dihydro-5H-dibenzo[a,c]cyclohepten-5-ylamine; and 2-{N-[(5S)-3,9,10,11-tetramethoxy-6,7-dihydro-5H-dibenzo[a,c]cyclohepten-5-yl]carbamoyloxy}ethyl disodium phosphate;

and pharmaceutically-acceptable salts, solvates or pro-drugs thereof.

Further particular compounds of the present invention include:

2-morpholinoethyl N-[(5S)-3,9,10,11-tetramethoxy-6,7-dihydro-5H-dibenzo[a,c]cyclohepten-5-yl]carbamate;

3-(1-methylpiperazin4-yl)propyl N-[(5S)-3,9,10,11-tetramethoxy-6,7-dihydro-5H-dibenzo[a,c]cyclohepten-5-yl]carbamate;

N-[(5S)-3,9,10,11-tetramethoxy-6,7-dihydro-5H-dibenzo[a,c]cyclohepten-5-yl]-2-[2-aminoacetylamino]acetamide;

2-(1-acetylpiperazin4-yl)ethyl-N-[(5S)-3,9,10,11-tetramethoxy-6-7-dihydro-5H-dibenzo[a,c]cyclohepten-5-yl]carbamate;

N-[(5S)-3,9,10,11-tetramethoxy-6-7-dihydro-5H-dibenzo[a,c]cyclohepten-5-yl]-4-(1-methylpiperazin4-yl)4-oxobutan-1-amide;

4-oxo-4-[(5S)-3,9,10,11-tetramethoxy-6,7-dihydro-5H-dibenzo[a,c]cyclohepten-5-yl]aminolbutyl disodium phosphate;

N-{N-[2-(imidazol-1-yl)ethyl]carbamoyl}-5(S)-3,9,10,11-tetramethoxy-6,7-dihydro-5H-dibenzo[a,c]cyclohepten-5-ylamine;

3-(1-acetylpiperazin-4-yl) propyl-N-[(5S)-3,9,10,11-tetramethoxy-6-7-dihydro-5H-dibenzo[a,c]cyclohepten-5-yl]carbamate;

N-1-[(5S)-3,9,10,11-tetramethoxy-6,7-dihydro-5H-dibenzo[a,c]cyclohepten-5-yl]carbamoyloxy]ethyl disodiumphosphate;

4-morpholino-4-oxobutyl-N-[(5S)-3,9,10,11-tetramethoxy-6,7-dihydro-5H-dibenzo[a-c]cyclohepten-5-yl]carbamate; and 4-(1-methylpiperazin4-yl)4-oxobutyl-N-[(5S)-3,9,10,11-tetramethoxy-6,7-dihydro-5H-dibenzo[a,c]cylcohepten-5-yl]carbamate;

and pharmaceutically-acceptable salts, solvates or pro-drugs thereof.

Synthesis of Compounds of the Formula (I)

Compounds of Formula (I) may be prepared by a number of processes as generally described hereinbelow and more specifically in the Examples hereinafter. Processes for the preparation of novel compounds of formula (I), are provided as a further feature of the invention and are as described hereinafter. Necessary starting materials may be obtained by standard procedures of organic chemistry. The preparation of such starting materials is described within the accompanying non-limiting Examples. Alternatively necessary starting materials are obtainable by analogous procedures to those illustrated which are within the ordinary skill of an organic chemist.

Thus according to another aspect of the invention, a compound of the Formula (I) may be formed by deprotecting a compound of the formula (I) wherein at least 1 functional group is protected. For example, amino, hydroxy, carboxy or phosphoryloxy groups may be protected during the reaction sequence used to prepare a compound of the formula (I).

Protecting groups may in general be chosen from any of the groups described in the literature or known to the skilled chemist as appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

A suitable protecting group for a hydroxy group is, for example, an arylmethyl group (especially benzyl), a triC$_{1-4}$alkysilyl group (especially trimethysilyl or tert-butyldimethylsilyl), an aryldi-C$_{1-4}$alkylsilyl group (especially dimethylphenylsilyl), a diarylC$_{1-4}$alkylsilyl group (especially tert-butyldiphenylsilyl), a C$_{1-4}$alkyl group (especially methyl), a C$_{2-4}$alkenyl group (especially allyl), a C$_{1-4}$alkoxymethyl group (especially methoxymethyl) or a tetrahydropyranyl group (especially tetrahydroyran-2-yl). The deprotection conditions for the above protecting groups will necessary vary with the choice of protecting group. Thus, for an example, arylmethyl group such as a benzyl group may be removed, for example, by hydrogenation over a catalyst such as palladium-on-charcoal. Alternatively a trialkylsilyl or an aryldialkylsilyl group such as tert-butyldimethylsilyl or a dimethylphenylsilyl group may be removed, for example, by treatment with a suitable acid such as hydrochloric, sulphuric, phosphoric or trifluoroacetic acid, or with an alkali metal or ammonium fluoride such as sodium fluoride or, preferably tetrabutylammonium fluroide. Alternatively an alkyl group may be removed, for example, by treatment with an alkali metal C$_{1-4}$alkylsulphide such as sodium thioethoxide or, for example, by treatment with an alkali metal diarylphosphide such as lithium diphenylphosphide or, for example, by treatment with a boron or aluminium trihalide such as boron tribromide. Alternatively a C$_{1-4}$alkoxymethyl group or tetrahydropyranyl group may be removed, for example, by treatment with a suitable acid such as hydrochloric or trifluoroacetic acid.

Alternatively a suitable protecting group for a hydroxy group is, for example, an acyl group, for example a $C_{2-4}$alkanoyl group (especially acetyl) or an aroyl group (especially benzoyl). The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide.

A suitable protecting group for an amino, imino or alkylamino group is, for example, an acyl group, for example a $C_{2-4}$alkanoyl group (especially acetyl), a $C_{1-4}$alkoxycarbonyl) group (especially methoxycarbonyl), ethoxycarbonyl or tert-butoxycarbonyl), an arylmethoxycarbonyl group (especially benzyloxycarbonyl) or an aroyl group (especially benzoyl). The deprotection conditions for the above protecting groups necessarily vary with the choice of protecting group. Thus, for example, an acyl group such as an alkanoyl, alkoxycarbonyl or aroyl group may be removed for example, by hydrolysis with a suitable base such as alkali metal hydroxide, for example lithium or sodium hydroxide. Alternatively an acyl group such as a tert-butoxycarbonyl group may be removed, for example, by treatment with a suitable acid such as hydrochloric, sulphuric or phosphoric acid or trifluoroacetic acid, and an arylmethoxycarbonyl group such as a benzyloxycarbonyl group may be removed, for example, by hydrogenation over a catalyst such as palladium-on-charcoal.

A suitable protecting group for a carboxy group is, for example, an esterifying group, for example a $C_{1-4}$alkyl group (especially methyl or ethyl) which may be removed, for example, by hydrolysis with a suitable base such as an alkali metal hydroxide, for example lithium or sodium hydroxide; or for example, a tert-butyl group which may be removed, for example, by treatment with a suitable acid such as hydrochloric, sulphuric or phosphoric acid or trifluoroacetic acid.

The reader is referred to Advanced Organic Chemistry, 4th Edition, by J. March, published by John Wiley & Sons 1992, for general guidance on reaction conditions and reagents and to Protective Groups in Organic Synthesis, $2^{nd}$ Edition, by T. Green et al., also published by John Wiley & Son, for general guidance on protecting groups.

In the following process description the symbols $R^1$–$R^7$, A, B, D, $R^a$ $R^b$, a and b are to be understood to represent those groups described above in relation to formulae (I) and (II) unless otherwise stated.

A compound of the formula (I), or a compound of the formula (I) wherein at least 1 functional group is protected, may be prepared using one of the following processes:

a) reacting a compound of the formula (X)

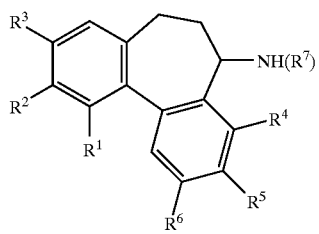

(X)

with a compound of the formula (XI):

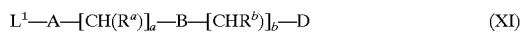

(XI)

wherein $L^1$ is a leaving group; or b) converting one compound of the formula (I) into another compound of the formula (I); or c) when a phosphoryloxy group is desired, reacting the corresponding hydroxy compound with a phosphoramidite;

wherein any functional groups are optionally protected. and thereafter if necessary:
  i) converting a compound of formula (I) into another compound of formula (I);
  ii) removing any protecting groups;
  iii) forming a pharmaceutically acceptable salt, solvate or pro-drug thereof.

The reaction between a compound of the formula (X) and a compound of the formula $L^1$—A—[CH($R^a$)]$_a$—B—[CH $R^b$)]$_b$—D is conveniently performed under standard acylation or sulphonylation conditions. $L^1$ is usually halogeno, for example chloro or bromo, hydroxy, mesyloxy, tosyloxy or an 'activated' hydroxy group. The precise conditions depending largely upon the nature of A.

For example, when —A— is —CO—, $L^1$ may be hydroxy and the reaction carried out in the presence of coupling agent such as dicyclohexylcarbodiimide or 1-(3-dimethylaminopropyl)-3-ethylcarbodiimide. Optionally, a base may be used, for example an organic base such as triethylamine. Suitable solvents are usually aprotic solvents, for example dimethylformamide, or chlorinated solvents, for example trichloromethane or dichloromethane. The temperature is usually in the range of about −30° C. to about 60° C., conveniently at or near ambient temperature.

When —A— is —C(O)O—, $L^1$ is usually an "activated" hydroxy group. That is a group which acts as a leaving group in the same way as hydroxy, but is more labile. It can be formed in situ. An example of an activated hydroxy group is 4-nitrophenoxy, which can be formed by reacting a hydroxy group (HO—[CH($R^a$)]$_a$—B—[CH($R^b$)]$_b$—D) with 4-nitrophenylchloroformate. This reaction is usually carried out in an organic solvent such as dichloromethane, acetonitrile or tetrahydrofuran, in a temperature range of about −20° C. to the reflux temperature of the solvent. In addition, organic base such as triethylamine or $\underline{N}$-methylmorpholine is normally present. Alternatively, a compound of the formula (X) can be reacted with 4-nitrophenylchloroformate and the resulting intermediate reacted with HO—[CH($R^a$)]$_a$—B—[CH($R^b$)]$_b$—D under similar conditions to those described above for the reaction of a compound of the formula (X) with a compound of the formula $L^2$—[CH($R^a$)]$_a$—B—[CH($R^b$)]$_b$—D wherein L2 is 4-nitrophenoxy.

When —A— is —CON($R^8$)—, $L^1$ is preferably halogeno, particularly chloro. Alternatively when —A— is —CONH—, a compound of the formula (X) can be reacted with an isocyanate of the formula C≡N—[CH($R^a$)]$_a$—B—[CH($R^b$)]$_b$—D. These reactions are conveniently carried out in the presence of a base, particularly an organic base, such as triethylamine, pyridine or $\underline{N}$-methylmorpholine, in a solvent such as an ether solvent, for example tetrahydrofuran, or in a chlorinated solvent, for example dichloromethane, at a temperature in the range from about −20° C. to the reflux temperature of the solvent. Alternatively, a compound of the formula (X) can be reacted with 4-nitrophenylchloroformate and the resulting intermediate reacted with $R^{17}NH_2$ under similar conditions to those described above for the reaction of a compound of the formula (X) with a compound of the formula $L^2$—[CH($R^a$)]$_a$—B—[CH($R^b$)]$_b$—D wherein $L^2$ is 4-nitrophenoxy.

When —A— is of the formula —$SO_2$— or —$SO_2N$($R^8$)—, $L^1$ is preferably halogeno, for example chloro. The reaction is conveniently carried out in the presence of a base such as dimethylaniline, in a chlorinated solvent such as trichloromethane and at a temperature in the range of −20°

C. to about 60° C., more preferably in pyridine, at a temperature in the range from −20° C. to about 60° C.

A compound of formula (I) may be prepared from another compound of formula (I) by chemical modification. Examples of chemical modifications include standard alkylation, arylation, heteroarylation, acylation, sulphonylation, phosphorylation, aromatic halogenation and coupling reactions. These reactions may be used to add new substituents or to modify existing substituents. Alternatively, existing substituents in compounds of formula (I) may be modified by, for example, oxidation, reduction, elimination, hydrolysis or other cleavage reactions to yield other compounds of formula (I).

Thus for example a compound of formula (I) containing an amino group may be acylated on the amino group by treatment with, for example, an acyl halide or anhydride in the presence of a base, for example a tertiary amine base such as triethylamine, in for example, a solvent such as a hydrocarbon solvent e.g. dichloromethane at a temperature in the range for example −30° C. to 120° C., conveniently at or near ambient temperature.

In another general example of an interconversion process, an amino group in a compound of formula (I) may be sulphonylated by treatment with, for example, an alkyl or aryl sulphonyl chloride or an alkyl or aryl sulphonic anhydride in the presence of a base, for example a tertiary amine base such as triethylamine, in for example a solvent such as a hydrocarbon solvent e.g. dichloromethane, at a temperature in the range for example −30° C. to 120° C., conveniently at or near ambient temperature.

In a further general example, a compound of formula (I) containing a hydroxy group can be converted into the corresponding dihydrogenphosphate ester by treatment with for example di-tert-butyl diisopropylphosphoramidite or di-tert-butyl diethylphosphoramidite in the presence of a suitable catalyst, for example tetrazole. A solvent such as an ether solvent, for example tetrahydrofuran can be used. The reaction is usually carried out at a temperature in the range −40° C. to 40° C., conveniently at or near ambient temperature, followed by treatment with an oxidising agent for example 3-chloroperoxy benzoic acid at a temperature in the range −78° C. to 40° C. preferably −40° C. to 10C. The resulting intermediate phosphate triester is treated with an acid, for example trifluoroacetic acid, in a solvent such as a chlorinated solvent e.g. dichloromethane at a temperature in the range −30° C. to 40° C., conveniently at or near 0° C., to give the compound of formula (I) containing a dihydrogenphosphate ester.

In a further general example a compound of formula (I) containing an amide can be hydrolysed by treatment with for example an acid such as hydrochloric acid in a solvent such as an alcohol, for example methanol at an elevated temperature conveniently at the reflux temperature.

In another general example an alkoxy group may be converted to the corresponding alcohol (OH) by reaction with boron tribromide in a solvent such as a chlorinated solvent e.g. dichloromethane at a low temperature e.g. around −78° C.

In a further general example a compound of formula (I) may be alkylated by reaction with a suitable alkylating agent such as an alkyl halide, an alkyl toluenesulphonate, an alkyl methanesulphonate or an alkyl triflate. The alkylation reaction can be carried out in the presence of a base, for example an inorganic base such as a carbonate e.g. caesium or potassium carbonate, a hydride such as sodium hydride or an alkoxide such as potassium t-butoxide, in a suitable solvent such as an aprotic solvent e.g. dimethylformamide or an ether solvent such as tetrahydrofuran, at a temperature of around −10° C. to 80° C.

In a further example, an unsubstituted ring nitrogen in a saturated heterocyclic ring may be acylated using similar reaction conditions to those described above for the acylation of an amino group.

Synthesis of Intermediates

A compound of the formula (X) may be known or prepared according to processes described in International Patent Application No. PCT/GB98/01977.

A compound of the formula (XI) may be known or prepared by methods known in the art. For example, when A is of the formula —C(O)O— and $L^1$ is 4-nitrophenyloxy, the compound of the formula (XI) may be formed by reacting a compound of the formula:

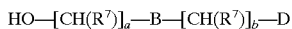

with 4-nitrophenyl chloroformate, in the presence of a base, preferably an organic base such as triethylamine, in an inert organic solvent such as dichloromethane. The reaction is usually carried out in a temperature range of −30° C. to 60° C., most commonly at around ambient temperature.

Acid addition salts of the compounds of formula (I) are prepared in a conventional manner by treating a solution or suspension of the free base of a compound of formula (I) with about one equivalent of a pharmaceutically acceptable acid. Salts of compounds of formula (I) derived from inorganic or organic bases are prepared in a conventional manner by treating a solution or suspension of the free acid of a compound of formula (I) with about one equivalent of a pharmaceutically acceptable organic or inorganic base. Alternatively both acid addition salts and salts derived from bases may be prepared by treatment of the parent compound with the appropriate ion-exchange resin in a standard fashion. Conventional concentration and recrystallistion techniques are employed in isolating the salts.

Compounds according to the invention are able to destroy vasculature that has been newly formed such as tumour vasculature while leaving unaffected normal, mature vasculature. The identification of compounds which selectively, and preferably potently, damage newly-formed vasculature is desirable and is the subject of the present invention. The ability of the compounds to act in this way may be assessed, for example, using one or more of the procedures set out below:

(a) Activity Against Tumour Vasculature Measured by Radioactive Tracer

This assay demonstrates the ability of compounds to damage selectively tumour vasculature.

Subcutaneous CaNT tumours were initiated by injecting 0.05 ml of a crude tumour cell suspension, approximately $10^6$ cells, under the skin overlying the rear dorsum of 12–16 week-old mice. The animals were selected for treatment after approximately 3–4 weeks, when their tumours reached a geometric mean diameter of 5.5–6.5 mm. Compounds were dissolved in sterile saline and injected intraperitoneally in a volume of 0.1 ml per 10 g body weight. Tumour perfusion was measured 6 hours after intraperitoneal administration in tumour, kidney, liver, skin, muscle, gut and brain by the $^{86}$RbCl extraction technique (Sapirstein, Amer. Jnl. Physiol., 1958, 193, 161–168). Tissue radioactivity measured 1 minute after an intravenous injection of $^{86}$RbCl was used to calculate relative blood flow as a proportion of cardiac output (Hill and Denekamp, Brit. Jnl. Radiol., 1982, 55, 905–913). Five animals were used in control and treated groups. Results were expressed as a percentage of the blood flow in the corresponding tissues in vehicle treated animals.
(b) Activity Against Tumour Vasculature Measured by Fluorescent Dye This assay demonstrates the ability of compounds to damage tumour vasculature.

Tumour functional vascular volume in CaNT tumour-bearing mice was measured using the fluorescent dye Hoechst 33342 according to the method of Smith et al (Brit. Jnl. Cancer 1988, 57, 247–253). Five animals were used in control and treated groups. The fluorescent dye was dissolved in saline at 6.25 mg/ml and injected intravenously at 10 mg/kg 24 hours after intraperitoneal drug treatment. One minute later, animals were killed and tumours excised and frozen; 10 μm sections were cut at 3 different levels and observed under UV illumination using an Olympus microscope equipped with epifluorescence. Blood vessels were identified by their fluorescent outlines and vascular volume was quantified using a point scoring system based on that described by Chalkley, (Jnl. Natl. Cancer Inst., 1943, 4, 47–53). All estimates were based on counting a minimum of 100 fields from sections cut at the 3 different levels.

The ability of the compounds to bind to preparations of mammalian tubulin can be evaluated by a number of methods available in the literature, for example by following temperature initiated tubulin polymerisation by turbidity in the absence and presence of the compound (for example O. Boye et al Med. Chem. Res., 1991, 1, 142–150).

The activity of N-[3-amino-9,10,11-trimethoxy-6,7-dihydro-5H-dibenzo[a,c]cyclohepten-5-yl]acetamide, (V. Fernholz Justus Liebigs Ann., 1950, 568, 63–72), against tumour vasculature was measured by the fluorescent dye method described above. This compound decreased perfused vascular volume by 88% relative to control when dosed at 50 mg/kg intraperitoneally. The $IC_{50}$ of this compound in a tubulin polymerisation assay was 58 micromolar (O. Boye et al Med. Chem. Res., 1991, 1, 142–150).
(c) HUVEC Detachment Assay This assay examined the effects of compounds on the adherence of HUVECs to tissue culture plasticware.

HUVECs were plated in 0.2% gelatin-coated 12 well tissue culture plates at a concentration of $3\times10^4$ cells per well in 1 ml TCS medium. After 24 hours, when the cells were at ~30% confluency, the cells were dosed with compound for 40 minutes at 37° C., 5% $CO_2$. After this incubation the medium containing drug was pipetted off, and the cells were then gently washed in 2 mls of HBSS (Hanks' Balanced Salt Solution purchased from Life Technologies Ltd, Paisley UK; Catalogue #24020–083) to remove any detached cells. The washing solution was then removed, and the adherent cells remaining were trypsinised using 300 μl of 1×Trypsin-EDTA solution (Life Technologies Ltd, Paisley, UK; Catalogue #43500-019) at ambient temperature for 2 minutes. The trypsinised cells were then made up to 1 ml with TCS Biologicals medium, then centrifuged at 200 rpm for 2 minutes. The cell pellet was then resuspended in a volume of 50 μl of TCS Biologicals medium. Total cell counts were obtained by counting the cells on a haemocytometer. The amount of cell detachment was calculated by comparing the number of cells remaining attached following treatment with the number in undosed control wells.
(d) Hras5 Necrosis Model NIH 3T3 fibroblasts transfected with Harvey ras, clone 5, (Hras5 cells) were kept in continual passage in Dulbecco's modifed Eagles medium (DMEM) containing 10% foetal bovine serum (FBS) and 1% glutamine, at 37° C. in a humidified incubator gassed with 7.5% carbon dioxide and 92.5% oxygen. Cells were implanted subcutaneously into the left flank of male nude mice (8–10 weeks of age) at an inoculum of $2\times10^5$ cells/mouse. Tumours were measured using calipers and randomised into groups of 2–4 mice between days 9–14 after implant. Mice were dosed with compounds, either intravenously or intraperitoneally, once on day of randomisation and culled 24 hours after dosing. Compounds were dissolved in 20% hydroxypropyl beta cyclodextrin in physiological saline at pH 7 and dosed in a volume of 0.1 ml per 10 g body weight. Tumours were excised, weighed and placed in buffered formalin. Area of necrosis in individual tumours was assessed from a haematoxylin/eosin stained-slide by a pathologist and scored from 0, meaning no significant change, to 10, meaning 91–100% necrosis. The activity of examples 5 and 7 (described hereinafter) against tumour vasculature was measured by the fluorescent dye method described hereinabove. Example 1 scored 6.0 at 100 m/kg and example 4 scored 3.2 at 50 m/kg.

According to a further aspect of the invention there is provided a pharmaceutical composition which comprises a compound of the formula (I) as defined hereinbefore or a pharmaceutically acceptable salt, solvate or pro-drug thereof, in association with a pharmaceutically acceptable excipient or carrier.

The composition may be in a form suitable for oral administration, for example as a tablet or capsule, for nasal administration or administration by inhalation, for example as a powder or solution, for parenteral injection (including intravenous, subcutaneous, intramuscular, intravascular or infusion) for example as a sterile solution, suspension or emulsion, for topical administration for example as an ointment or cream or for rectal administration for example as a suppository. In general the above compositions may be prepared in a conventional manner using conventional excipients.

The compositions of the present invention are advantageously presented in unit dosage form. The compound will normally be administered to a warm-blooded animal at a unit dose within the range 5–5000 mg per square meter body area of the animal, i.e. approximately 0.1–100 mg/kg. A unit dose in the range, for example, 1–100 mg/kg, preferably 1–50 mg/kg is envisaged and this normally provides a therapeutically-effective dose. A unit dose form such as a tablet or capsule will usually contain, for example 1–250 mg of active ingredient.

As stated above the size of the dose required for the therapeutic or prophylactic treatment of a particular disease state will necessarily be varied depending on the host treated, the route of administration and the severity of the illness being treated. Preferably a daily dose in the range of 1–50 mg/kg is employed. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided a compound of the formula (I) or a pharmaceutically acceptable salt, solvate or pro-drug thereof as defined hereinbefore for use in a method of treatment of the human or animal body by therapy.

A further feature of the present invention is a compound of formula (I), or a pharmaceutically acceptable salt, solvate or pro-drug thereof, for use as a medicament, conveniently a compound of formula (I), or a pharmaceutically acceptable salt, solvate or pro-drug thereof, for use as a medicament for producing a vascular damaging effect in a warm-blooded animal such as a human being.

Thus according to a further aspect of the invention there is provided the use of a compound of the formula (I), or a pharmaceutically acceptable salt, solvate or pro-drug thereof in the manufacture of a medicament for use in the production of a vascular damaging effect in a warm-blooded animal such as a human being.

According to a further feature of the invention there is provided a method for producing a vascular damaging effect in a warm-blooded animal, such as a human being, in need of such treatment which comprises administering to said animal an effective amount of a compound of formula (I) or a pharmaceutically acceptable salt, solvate or pro-drug thereof as defined herein before.

According to a further aspect of the present invention there is provided a compound of formula (I) or pharmaceutically-acceptable salt, solvate or pro-drug thereof, preferably in the form of a pharmaceutical composition, when dosed in divided doses (also known as split doses) produces a greater anti-tumour effect than when a single dose is given.

Anti-tumour effects of a method of treatment of the present invention include but are not limited to, inhibition of tumour growth, tumour growth delay, regression of tumour, shrinkage of tumour, increased time to re-growth of tumour on cessation of treatment, slowing of disease progression. It is expected that when a method of treatment of the present invention is administered to a warm-blooded animal such as a human, in need of treatment for cancer involving a solid tumour, said method of treatment will produce an effect, as measured by, for example, one or more of: the extent of the anti-tumour effect, the response rate, the time to disease progression and the survival rate.

According to a further aspect of the present invention there is provided a method for the production of a vascular damaging effect in a warm-blooded animal such as a human, which comprises administering to said animal in divided doses an effective amount of a compound of formula (I) or pharmaceutically-acceptable salt, solvate or pro-drug thereof, preferably in the form of a pharmaceutical composition.

According to a further aspect of the present invention there is provided a method for the treatment of a cancer involving a solid tumour in a warm-blooded animal such as a human, which comprises administering to said animal in divided doses an effective amount of a compound of formula (I) or pharmaceutically-acceptable salt, solvate or pro-drug thereof, preferably in the form of a pharmaceutical composition.

According to a further aspect of the present invention there is provided a medicament comprising two or more fractions of doses of a compound of formula (I) or pharmaceutically-acceptable salt, solvate or pro-drug thereof, preferably in the form of a pharmaceutical composition, which together add up to a total daily dose, for administration in divided doses for use in a method of treatment of a human or animal body by therapy.

According to a further aspect of the present invention there is provided a kit comprising two or more fractions of doses of a compound of formula (I) or pharmaceutically-acceptable salt, solvate or pro-drug thereof, preferably in the form of a pharmaceutical composition, which together add up to a total daily dose, for administration in divided doses.

According to a further aspect of the present invention there is provided a kit comprising:

a) two or more fractions of doses of a compound of formula (D) or pharmaceutically-acceptable salt, solvate or pro-drug thereof, which together add up to a total daily dose, in unit dosage forms for administration in divided doses; and b) container means for containing said dosage forms.

According to a further aspect of the present invention there is provided a kit comprising:

a) two or more fractions of doses of a compound of formula (I) or pharmaceutically-acceptable salt, solvate or pro-drug thereof, which together add up to a total daily dose, together with a pharmaceutically acceptable excipient or carrier, in unit dosage forms; and b) container means for containing said dosage forms.

According to a further aspect of the present invention there is provided the use of compound of formula (I) or pharmaceutically-acceptable salt, solvate or pro-drug thereof in the manufacture of a medicament for administration in divided doses for use in the production of a vascular damaging effect in a warm-blooded animal such as a human.

According to a further aspect of the present invention there is provided the use of a compound of formula (I) or pharmaceutically-acceptable salt, solvate or pro-drug thereof in the manufacture of a medicament for administration in divided doses for use in the production of an anti-cancer effect in a warm-blooded animal such as a human.

According to a further aspect of the present invention there is provided the use of a compound of formula (I) or pharmaceutically-acceptable salt, solvate or pro-drug thereof in the manufacture of a medicament for administration in divided doses for use in the production of an anti-tumour effect in a warm-blooded animal such as a human.

Divided doses, also called split doses, means that the total dose to be administered to a warm-blooded animal, such as a human, in any one day period (for example one 24 hour period from midnight to midnight) is divided up into two or more fractions of the total dose and these fractions are administered with a time period between each fraction of about greater than 0 hours to about 10 hours, preferably about 1 hour to about 6 hours, more preferably about 2 hours to about 4 hours. The fractions of total dose may be about equal or unequal.

Preferably the total dose is divided into two parts which may be about equal or unequal.

The time intervals between doses may be for example selected from: about 1 hour, about 1.5 hours, about 2 hours, about 2.5 hours, about 3 hours, about 3.5 hours, about 4 hours, about 4.5 hours, about 5 hours, about 5.5 hours and about 6 hours.

The time intervals between doses may be any number (including non-integers) of minutes between greater than 0 minutes and 600 minutes, preferably between 45 and 375 minutes inclusive. If more than two doses are administered the time intervals between each dose may be about equal or unequal.

Preferably two doses are given with a time interval in between them of greater than or equal to 1 hour and less than 6 hours.

More preferably two doses are given with a time interval in between them of greater than or equal to two hours and less than 5 hours.

Yet more preferably two doses are given with a time interval in between them of greater than or equal to two hours and less than or equal to 4 hours.

Particularly the total dose is divided into two parts which may be about equal or unequal with a time interval between doses of greater than or equal to about two hours and less than or equal to about 4 hours.

More particularly the total dose is divided into two parts which may be about equal with a time interval between doses of greater than or equal to about two hours and less than or equal to about 4 hours.

For the avoidance of doubt the term 'about' in the description of time periods means the time given plus or minus 15 minutes, thus for example about 1 hour means 45 to 75 minutes,. about 1.5 hours means 75 to 105 minutes. Elsewhere the term 'about' has its usual dictionary meaning.

The antiangiogenic treatment defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the antiangiogenic treatment defined hereinbefore may be: surgery, radiotherapy or chemotherapy. Such chemotherapy may include the following categories of therapeutic agent:

(i) other antiangiogenic agents that work by different mechanisms from those defined hereinbefore (for example linomide, inhibitors of integrin αvβ3 function, angiostatin, endostatin, razoxin, thalidomide) and including vascular endothelial growth factor (VEGF) receptor tyrosine kinase inhibitors (RTKIs) (for example those described in International Patent Applications Publication Nos. WO 97/22596, WO 97/30035, WO 97/32856 and WO 98/13354 the entire disclosure of which documents is incorporated herein by reference);

(ii) cytostatic agents such as antioestrogens (for example tamoxifen, toremifene, raloxifene, droloxifene, iodoxyfene), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide), inhibitors of testosterone 5α-dihydroreductase (for example finasteride), anti-invasion agents (for example metalloproteinase inhibitors like marimastat and inhibitors of urokinase plasminogen activator receptor function) and inhibitors of growth factor function, (such growth factors include for example epidermal growth factor (EGF), platelet derived growth factor and hepatocyte growth factor such inhibitors include growth factor antibodies, growth factor receptor antibodies, tyrosine kinase inhibitors and serine/threonine kinase inhibitors);

(iii) biological response modifiers (for example interferon);

(iv) antibodies (for example edrecolomab); and (v) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincristine and taxoids like taxol, taxotere); enzymes (for example asparaginase); thymidylate synthase inhibitors (for example raltitrexed); topoisomerase inhibitors (for example epipodophyllotoxins like etoposide and teniposide, amsacrine, topotecan, irinotecan).

As stated above the compounds defined in the present invention are of interest for their vascular damaging effects. Such compounds of the invention are expected to be useful in the prophylaxis and treatment of a wide range of disease states where inappropriate angiogenesis occurs including cancer, diabetes, psoriasis, rheumatoid arthritis, Kaposi's sarcoma, haemangioma, acute and chronic nephropathies, atheroma, arterial restenosis, autoimmune diseases, acute inflammation, endometriosis, dysfunctional uterine bleeding and ocular diseases with retinal vessel proliferation. In particular such compounds of the invention are expected to slow advantageously the growth of primary and recurrent solid tumours of, for example, the colon, breast, prostate, lungs and skin.

In addition to their use in therapeutic medicine, the compounds of formula (I) and their pharmaceutically acceptable salts, solvates or pro-drugs are also useful as pharmacological tools in the development and standardisation of in vitro and in vivo test systems for the evaluation of the effects of vascular damaging agents in laboratory animals such as cats, dogs, rabbits, monkeys, rats and mice, as part of the search for new therapeutic agents.

It is to be understood that where the term "ether" is used anywhere in this specification it refers to diethyl ether.

The invention will now be illustrated in the following non-limiting Examples in which, unless otherwise stated:

(i) evaporations were carried out by rotary evaporation in vacuo and work-up procedures were carried out after removal of residual solids such as drying agents by filtration;

(ii) operations were carried out at ambient temperature, that is in the range 18–25° C. and under an atmosphere of an inert gas such as argon or nitrogen;

(iii) yields are given for illustration only and are not necessarily the maximum attainable;

(iv) the structures of the end-products of the formula (I) were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet, quin, quintet;

(v) intermediates were not generally fully characterised and purity was assessed by thin layer chromatography (TLC), high-performance liquid chromatography (HPLC), infra-red (IR) or NMR analysis;

| Abbreviations | |
|---|---|
| 4-Dimethylaminopyridine | DMAP |
| 1-(3-Dimethylaminopropyl)-3-ethylcarbodiimide hydrochloride | EDCI |
| Dimethyl sulphoxide | DMSO |
| Trifluoroacetic acid | TFA |

EXAMPLE 1

N-[(5S)-3,9,10,11-Tetramethoxy-6,7-dihydro-5H-dibenzo[a,c]cyclohepten-5-yl]-2-[2-aminoacetylamino]acetamide

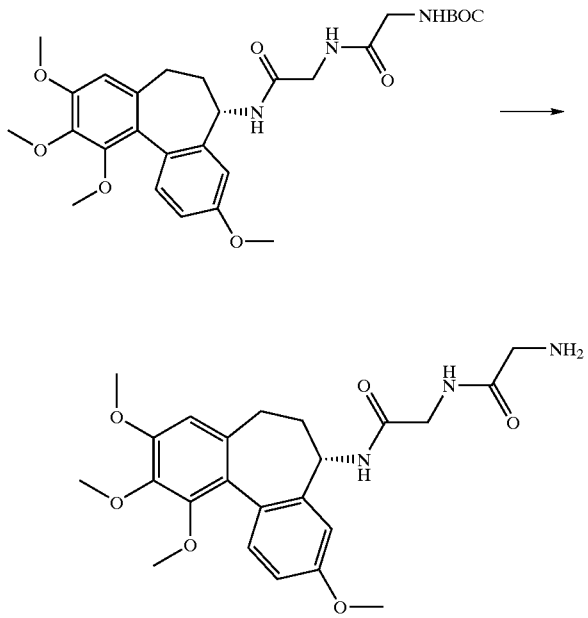

A solution of N-[(5S)-3,9,10,11-tetramethoxy-6,7-dihydro-5H-dibenzo[a,c]cyclohepten-5-yl]-2-[2-(butoxycarbonylamino)acetylamino]acetamide (0.9 g; 0.64 mmol) in dichloromethane (6 ml) was treated with TFA (6 ml) at ambient temperature for 0.5 hour. After evaporation to dryness, the residue was neutralised to pH 6.5 with solid sodium hydrogen carbonate and purified on reverse phase silica eluting with a gradient of 30–40% methanol/ammonium carbonate buffer (2 g/l, pH 7). The appropriate fractions were evaporated to dryness and triturated in ether to give the title compound.

Yield: 65%; $^1$H NMR (DMSO-$d_6$): 1.88–2.21 (m, 3H); 2.58 partially obscured by DMSO peak (m, 1H); 3.10 (s, 2H); 3.46 (s, 3H); 3.79 (s, 3H); 3.82 (s, 3H); 3.83 (s, 3H); 3.84 (s, 3H); 4.47–4.58 (m, 1H); 6.77 (s, 1H); 6.87 (dd, 1H); 6.91 (d, 1H); 7.25 (d, 1H); 8.06 (m, 1H); 8.41 (d, 1H). MS-ESI: 444 [MH]$^+$.

| Elemental analysis | Found | C 59.14 | H 6.44 | N 9.08 |
|---|---|---|---|---|
| $C_{23}H_{29}N_3O_6$, 1.2 $H_2O$ | Requires | C 59.39 | H 6.80 | N 9.03 |

The starting material was prepared as follows:

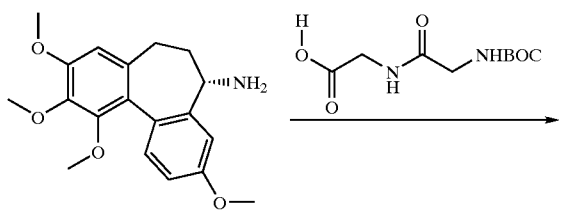

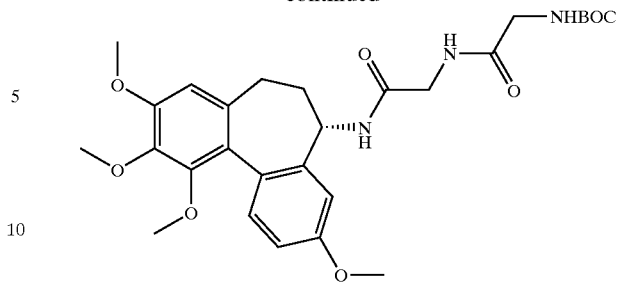

A solution of (5S)-3,9,10,11-tetramethoxy-6,7-dihydro-5H-dibenzo[a,c]cyclohepten-5-ylamine [Collect. Czech. Chem. Commun. 1999, 64(2), 217–228] (0.329 g; 1.36 mmol), EDCI (0.230 g; 1.2 mmol); DMAP (0.025 g, 0.2 mmol) and 2[2-(tert-butoxycarbonylamino)acetylamino] acetic acid (0.189 g; 1.2 mmol) in dichloromethane was stirred under argon atmosphere overnight. The resulting precipitate was filtered and washed with ether to give N-[(5S)-3,9,10,11-tetramethoxy-6,7-dihydro-5H-dibenzo[a,c]cyclohepten-5-yl]-2-[2-(butoxycarbonylamino)acetylamino]acetamide as a whit solid.

Yield: 65%. $^1$H NMR (DMSO-$d_6$): 1.33 (s, 9H); 1.94–2.24 (m, 3H); 2.97–3.08 (m, 1H); 3.35 (s, 3H); 3.56 (t, 3H); 3.71–3.77 (m, 1H); 3.75 (s, 3H); 3.78 (s, 3H); 3.80 (s, 3H); 4.48–4.59 (m, 1H); 6.79 (s, 1H); 6.87 (dd, 1H); 6.93 (d, 1H); 7.14 (t, 1H); 7.25 (d, 1H); 8.17 (t, 1H); 8.21 (d, 1H). MS-ESI: 544 [MH]$^+$.

EXAMPLE 2

4-oxo-4-[(5S)-3,9,10,11-Tetramethoxy-6,7-dihydro-5H-dibenzo[a,c]cyclohepten-5-yl]amino]butyl Disodium Phosphate

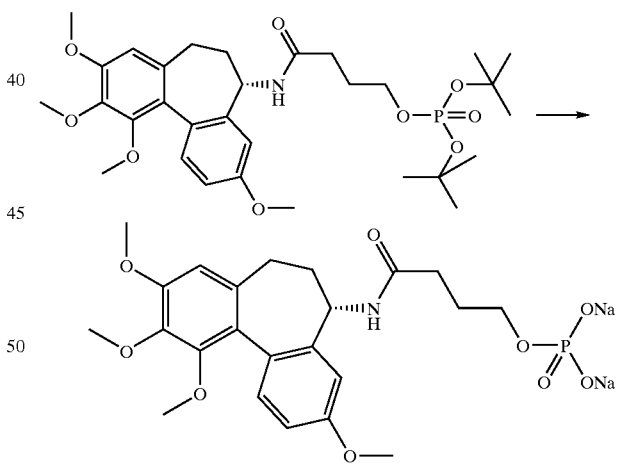

A solution of N-[(5S)-3,9,10,11-tetramethoxy-6,7-dihydro-5H-dibenzo[a,c]cyclohepten-5-yl]-4-[di(tert-butoxy)phosphoryloxy]butanamide (0.529 g; 0.892 mmol) in a mixture of (12N) HCl (5 ml) and dioxan (25 ml) was stirred under argon atmosphere for 4 hours. After evaporation of the dioxan, the pH was adjusted at 7.2 with sodium hydroxide solution (2N) and the residue purified on HP20SS resin eluting with a 0–40% gradient of methanol/water to give the title compound after freeze drying.

Yield: 75%; $^1$H NMR (DMSO-$d_6$): 1.71–2.36 (m, 7H); 2.58 partially obscured by DMSO peak (m, 1H); 3.49 (s, 3H); 3.78–3.85 (m, 11H); 5.20 (dd, 1H); 5.00 (s, 1H); 6.77 (s, 1H); 6.88 (dd, 1H); 6.91 (d, 1H); 6.26 (d, 1H).

The starting material was prepared as follows:

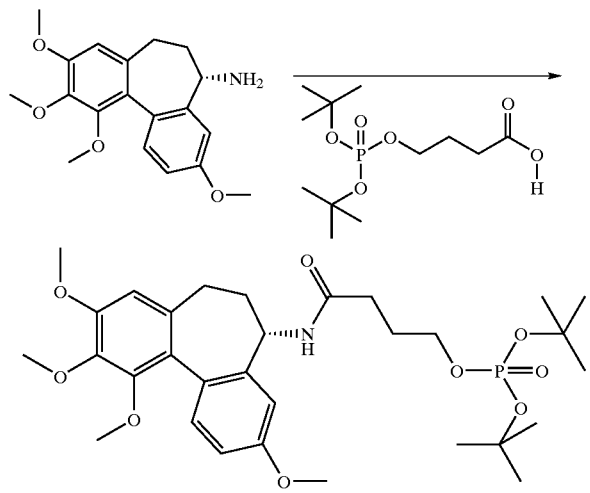

N-[(5S)-3,9,10,11-tetramethoxy-6,7-dihydro-5H-dibenzo[a,c]cyclohepten-5-yl]-4-[di-(tert-butoxy)phosphoryloxy]butanamide was prepared using a similar method to that of Example 1 by reacting (SS)-3,9,10,11-tetramethoxy-6,7-dihydro-5H-dibenzo[a,c]cyclohepten-5-ylamine with 4-[di(tert-butoxy)phosphoryloxy]butanoic acid.

Yield: 89%; $^1$H NMR (DMSO-$d_6$): 1.40 (s, 18H); 1.80 (t, 2H); 1.82–1.94 (m, 1H); 2.00–2.20 (m, 2H; 2.23–2.33 (m, 2H); 2.52–2.58 (m, 1H); 3.48 (s, 3H); 3.78 (s, 3H); 3.80–3.85 (m, 8H); 4.50–4.59 (m, 1H); 6.78 (s, 1H); 6.89 (dd, 1H); 6.90 (d, 1H); 7.26 (d, 1H); 8.42 (d, 1H).

EXAMPLE 3

N-{N-[2-(Imidazol-1-yl)ethyl]carbamoyl}-5(S)-3,9,10,11-tetramethoxy-6,7-dihydro-5H-dibenzo[a,c]cyclohepten-5-ylamine

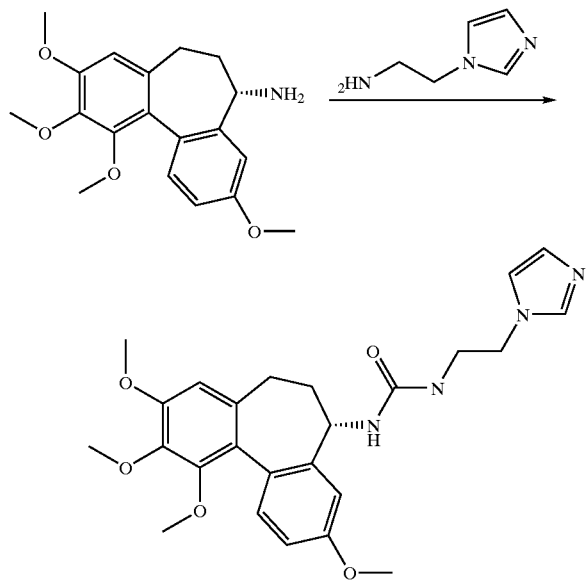

A solution of (5S)-3,9,10,11-tetramethoxy-6,7-dihydro-5H-dibenzo[a,c]cyclohepten-5-ylamine (0.263 g; 0.8 mmol), 4-nitrophenol chloroformate (0.177 g; 0.88 mmol) and triethylamine (0.123 ml; 0.88 mmol) in dichloromethane was stirred under argon atmosphere for 1 hour. 2-(Imidazol-1-yl)ethylamine (0.145 ml; 1.2 mmol) was added. After stirring for 2 hours, the mixture was evaporated to dryness and the residue purified on reverse phase silica eluting with a 40–60% gradient of methanol/ammonium carbonate buffer (2 g/l, pH 7) to give the title compound after evaporation and trituration in ether.

Yield: 52%. $^1$H NMR (DMSO-$d_6$): 1.66–1.77 (m, 1H); 1.97–2.10 (m, 1H); 2.13–2.25 (m, 1H); 2.53 partially obscured by DMSO peak (m, 1 H); 3.12–3.32 (m, 2H); 3.47 (s, 3H); 3.77 (s, 3H); 3.79 (s, 3H); 3.83 (s, 1H); 3.94 (t, 3H); 4.32–4.42 (m, 1H); 5.97 (t, 1H); 6.63 (d, 1H); 6.77 (s, 1H); 6.83–6.92 (m, 3H); 7.11 (s, 1H); 7.24 (d, 1H); 7.54 (s, 1H). MS-ESI: 481 [MH]$^+$.

| Elemental analysis | Found | C 64.68 | H 6.89 | N 11.55 |
|---|---|---|---|---|
| $C_{23}H_{32}N_4O_5$ | Requires | C 64.98 | H 6.71 | N 11.66 |

EXAMPLE 4

2-{N-[(5S)-3,9,10,11-Tetramethoxy-6,7-dihydro-5H-dibenzo[a,c]cyclohepten-5-yl]carbamoyloxy}ethyl Disodium Phosphate

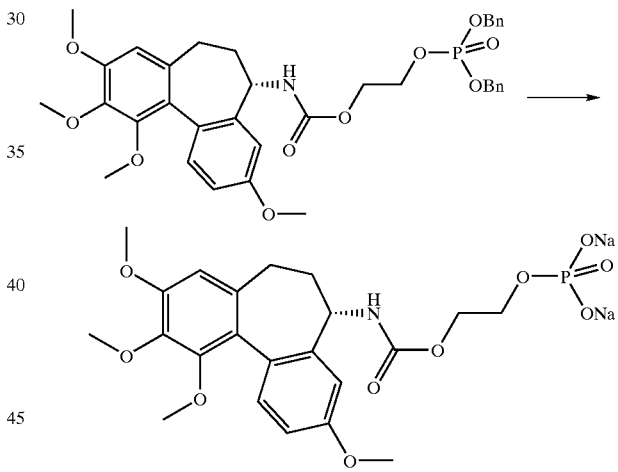

A solution of 2-[di-(benzyloxy)phosphoryloxy]ethyl N-[(5S)-3,9,10,11-tetramethoxy-6,7-dihydro-5H-dibenzo[a,c]cyclohepten-5-yl]carbamate (0.576 g; 0.85 mmol) in solution in methanol (10 ml) and ethyl acetate (5 ml) was hydrogenated in the presence of 10% C/Pd (0.165 mg) for 4 hours. After filtration on celite and evaporation, the residue was purified on HP2O SS resin eluting with a 0–80% gradient of methanol/distilled water. The pH of the corresponding fractions was adjusted at 8 with aqueous sodium hydroxide solution (2N), after evaporation of the methanol. After freeze drying the title compound was obtained as a white solid.

Yield: 83%; $^1$H NMR (DMSO-$d_6$+TFA-d): 1.85–1.97 (m, 1H); 1.98–2.09 (m, 1H); 2.13–2.27 (m, 1H); 2.42–2.52 (m, 1H); 3.48 (s, 3H); 3.79 (s, 3H); 3.80 (s, 3H); 3.84 (s, 3H); 3.98 (m, 2H); 4.03–4.18 (m, 2H); 4.04–4.17 (m, 2H); 4.24–4.35 (m, 1H); 6.77 (s, 1H); 6.89 (dd, 1H); 6.96 (d, 1H); 7.27 (d, 1H). MS-ESI: 498 [MH]$^+$.

The starting material was prepared as follows:

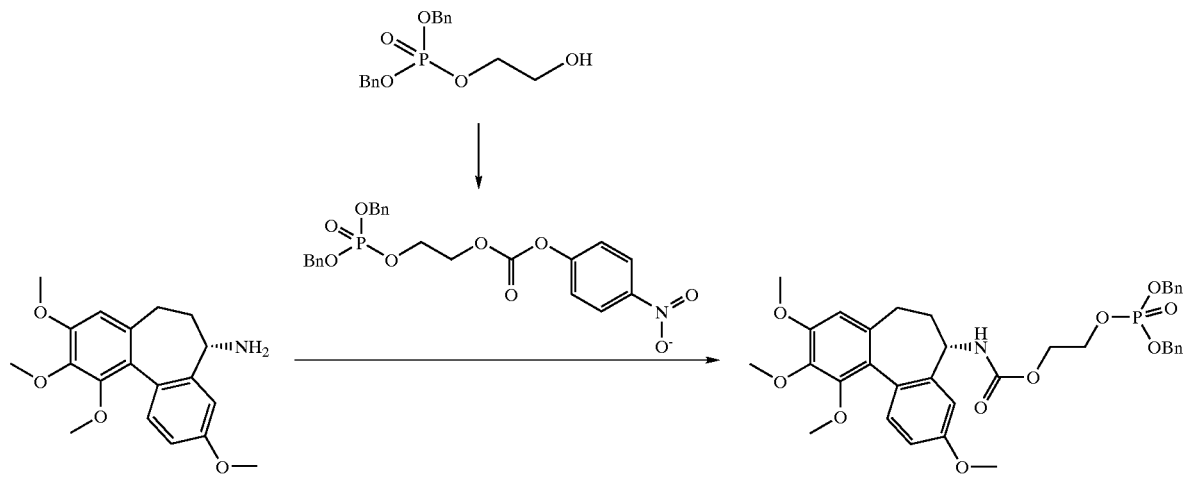

4-Nitrophenyl chloroformate (1.01 g; 5.04 mmol) was added at 0° C. under argon atmosphere to a solution of 2-[di(benzyloxy)phosphoryloxy]ethanol (1.62 g; 5.09 mmol) and triethylamine (0.7 ml; 5 mmol) in dichloromethane (20 ml). The mixture was stirred at ambient temperature for 30 minutes, evaporated and purified by flash chromatography, eluting with petroleum ether/ethyl acetate (40/60) to give 2-[di(benzyloxy)phosphoryloxy]ethyl 4-nitrophenyl carbonate.

Yield: 45%; $^1$HNMR (CDCl$_3$): 4.214.30 (m, 2H); 4.41 (m, 2H); 5.01–5.15 (m, 4H); 7.29–7.42 (m, 12H); 8.25 (d, 2H).

A solution of (5S)-3,9,10,11-tetramethoxy-6,7-dihydro-5H-dibenzo[a,c]cyclohepten-5-ylamine (0.329; 1 mmol) and 2-[di-(benzyloxy)phosphoryloxy]ethyl 4-nitrophenyl carbonate (0.633 g; 1.3 mmol) in acetonitrile (8 ml) was heated at 65° C., under argon atmosphere for 8 hours. After evaporation to dryness, the residue was purified by flash chromatography eluting with a 50–80% gradient of ethyl acetate/petroleum ether to give 2-[di(benzyloxy)phosphoryloxy]ethyl N-[(5S)-3,9,10,11-tetramethoxy-6,7-dihydro-5H-dibenzo[a,c]cyclohepten-5-yl]carbamate.

Yield: 85%; $^1$H NMR (DMSO-d$_6$): 1.81–1.93 (m, 1H); 1.94–2.06 (m, 1H); 2.06–2.20 (m, 1H) 2.40–2.52 (m, 1H); 3.43 (s, 3H); 3.73 (s, 3H); 3.77 (s, 3H); 3.82 (s, 3H); 4.11 (m, 4H); 4.20–4.33 (m, 4H); 5.02 (d, 4H); 6.76 (s, 1H); 6.86-dd, 1H); 6.93 (d, 1H); 7.25 (d, 1H), 7.35 (s, 10H); 7.99 (d, 1H).

EXAMPLE 5

2-Morpholinoethyl N-[(5S)-3,9,10,11-tetramethoxy-6,7-dihydro-5H-dibenzo[a,c]cyclohepten-5-yl]carbamate

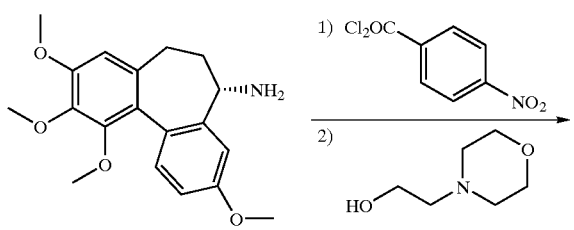

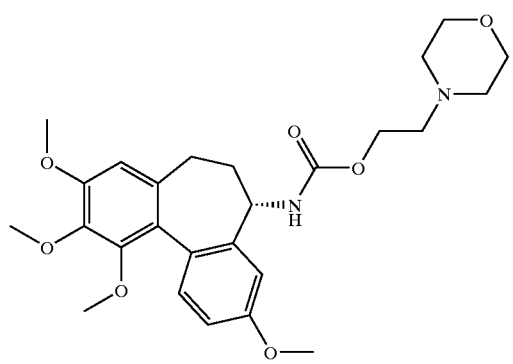

A solution of (5S)-3,9,10,11-tetramethoxy-6,7-dihydro-5H-dibenzo[a,c]cyclohepten-5-ylamine [Collect. Czech. Chem. Commun. 1999, 64(2), 217–228] (0.263 g; 0.8 mmol), 4-nitrophenylchloroformate (0.177 g; 0.88 mmol) and triethylamine (0.123 ml; 0.88 mmol) in acetonitrile (5 ml) was stirred under argon atmosphere for 2 hours at ambient temperature; 4-(2-hydroxyethyl)morpholine (0.145 ml; 1.2 mmol) in solution in acetonitrile (2 ml) was then added to the above solution. The mixture was heated at 60° C. overnight. After evaporation to dryness, the residue was purified by flash chromatography, eluted with ethanol/dichloromethane (4/96) to give the title compound.

Yield: 64%; $^1$H NMR Spectrum (DMSO-d$_6$+AcO-d$_4$): 1.82–2.31 (m, 3H); 2.44 (m, 4H); 2.49 (m, 2H); 2.57 partially obscured by DMSO peak (m, 1H); 3.47 (s, 3H); 3.56 (m, 4H); 3.78 (s, 3H); 3.79 (s, 3H); 3.83 (s, 3H); 4.03 (m, 2H); 4.17–4.33 (m, 1H); 6.76 (s, 1H); 6.88 (dd, 1H); 6.93 (d, 1H); 7.26 (d, 1H); 7.86 (d, 1H). MS-ESI: 487 [MH]$^+$.

| Elemental analysis: | Found | C 63.38 | H 7.04 | N 5.74 |
|---|---|---|---|---|
| $C_{26}H_{34}N_2O_7$,0.3 H$_2$O | Requires | C 63.48 | H 7.09 | N 5.69 |

EXAMPLE 6
3-(1-Methylpiperazin-4-yl)propyl N-[(5S)-3,9,10,11-tetramethoxy-6,7-dihydro-5H-dibenzo[a,c]cyclohepten-5-yl]carbamate

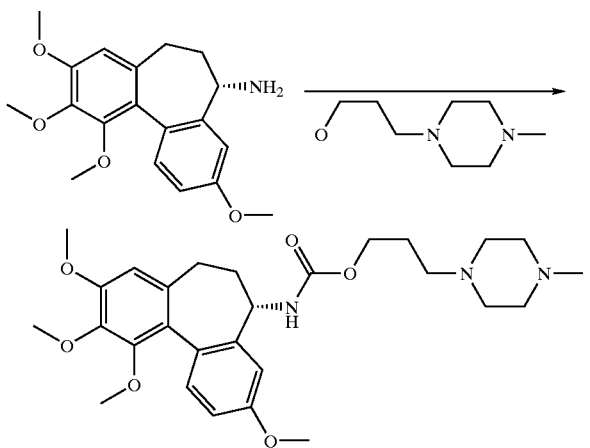

Using a similar procedure to that described for Example 5, (5S)-3,9,10,11-tetramethoxy-6,7-dihydro-5H-dibenzo[a,c]cyclohepten-5-ylamine was reacted with 4-(3-hydroxypropyl)-1-methylpiperazine to give the title compound.

Yield: 40%. $^1$H NMR (DMSO-$d_6$): 1.62–2.44 (m, 20H); 2.54 partially obscured by DMSO peak (m, 1H); 3.46 (s, 3H); 3.77 (s, 3H); 3.78 (s, 3H); 3.82 (s, 3H); 6.78 (s, 1H); 6.89 (dd, 1H); 6.93 (d, 1H); 7.27 (d, 1H); 7.80 (d, 1H). MS-ESI: 514 [MH]$^+$.

| Elemental analysis: | Found | C 65.42 | H 7.54 | N 8.18 |
|---|---|---|---|---|
| $C_{28}H_{39}N_3O_6$ | Requires | C 65.48 | H 7.65 | N 8.18 |

EXAMPLE 7
2-(1-Acetylpiperazin-4-yl)ethyl-N-[(5S)-3,9,10,11-tetramethoxy-6,7-dihydro-5H-dibenzo[a,c]cyclohepten-5-yl]carbamate

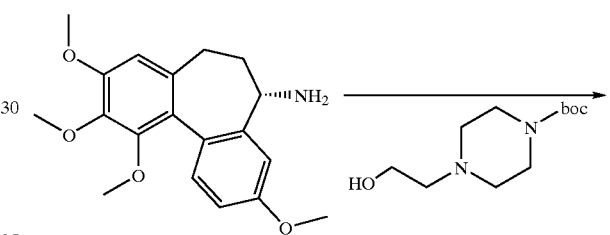

A solution of 2-(piperazin4-yl)ethyl-N-[(5S)-3,9,10,11-tetramethoxy-6-7-dihydro-5H-dibenzo[a,c]cyclohepten-5-yl]carbamate (0.255 g; 0.525 mmol), acetyl chloride (0.038 ml; 0.53 mmol) and triethylamine (0.073 ml; 0.525 mmol) in dichloromethane (10 ml) was stirred at ambient temperature under argon atmosphere for 2 hours. After evaporation to dryness, the residue was purified by flash chromatography, eluting with dichhloromethane/ethanol (93/7) to give the title compound.

Yield: 90%; $^1$H NMR (DMSO-$d_6$): 1.81–2.32 (m, 3H); 1.97 (s, 3H); 2.33 (m, 2H); 2.40 (m, 2H); 2.47 partially obscured by DMSO peak (m, 2H); 2.58 partially obscured by DMSO peak (m, 1H); 3.38 (m, 4H); 3.46 (s, 3H); 3.77 (m, 3H); 3.80 (s, 3H); 3.82 (s, 3H); 3.92–4.10 (m, 2H); 4.204.30 (m, 1H); 6.77 (s, 1H); 6.88 (dd, 1H); 6.92 (d, 1H); 7.25 (d, 1H); 7.87 (d, 1H). MS-ESI: 528 [MH]$^+$.

| Elemental analysis: | Found | C 63.21 | H 7.30 | N 7.86 |
|---|---|---|---|---|
| $C_{28}H_{37}N_3O_7$ | Requires | C 63.52 | H 7.08 | N 7.94 |

The starting material was prepared as follows:

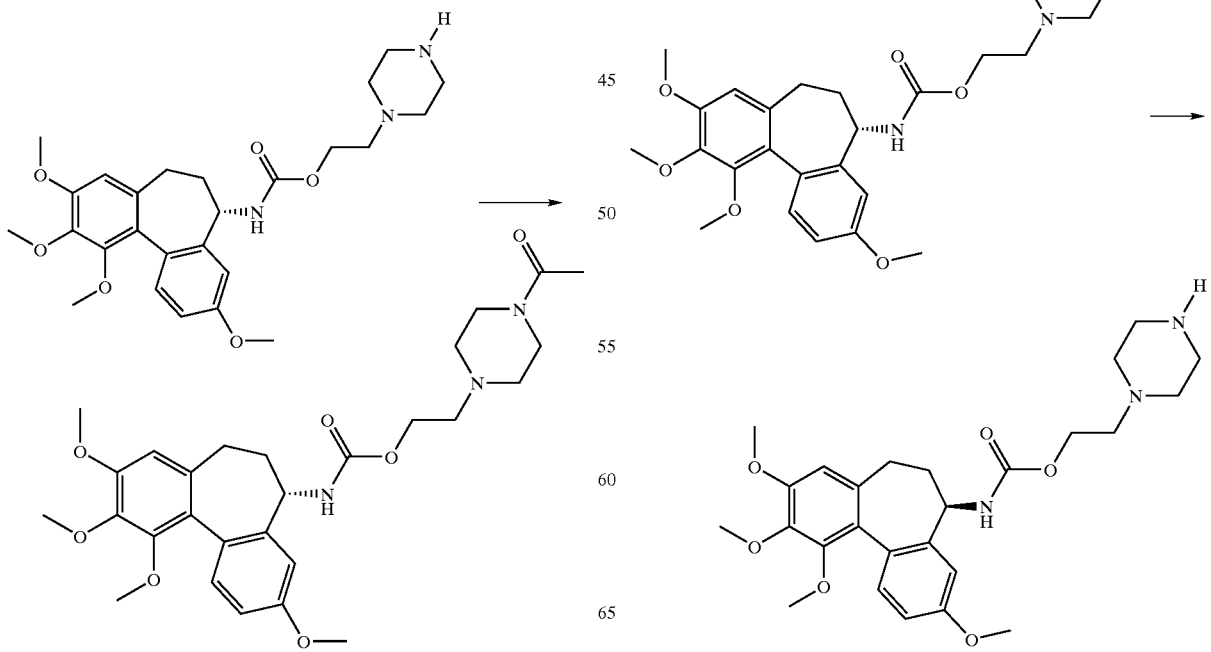

2-(1-tert-Butoxycarbonylpiperazin4-yl)ethyl-N-[(5S)-3,
9,10,11-tetramethoxy-6,7-dihydro-5H-dibenzo[a,c]
cyclohepten-5-yl]carbamate was prepared using a similar
method to that described for Example 1, but using 2-[1-
(tert-butoxycarbonyl)piperazin-4-yl]ethanol.

Yield: 75%; $^1$H NMR (DMSO-d$_6$): 1.78–1.94 (m, 1H);
1.95–2.07 (m, 1H); 2.10–2.23 (m, 1H); 2.30 (m, 4H);
2.38–2.53 (m, 3H); 2.65 (t, 2H); 3.46 (s, 3H); 3.77 (s, 3H);
3.78 (s, 3H); 3.82 (s, 3H); 3.99 (t, 2H); 4.20–4.32 (m, 1H);
6.77 (s, 1H); 6.88 (dd, 1H); 6.92 (d, 1H); 7.25 (d, 1H); 7.86
(d, 1H).

2-(-1-tert-Butoxycarbonylpiperazin-4-yl)ethyl-N-[(5S)-3,
9,10,11-tetramethoxy-6,7-dihydro-5H-dibenzo[a,c]
cyclohepten-5-yl]carbamate (0.617 g; 1.05 mmol) in dichloromethane (10 ml) was treated with TFA (5 ml) at ambient temperature for 1 hour. After evaporation to dryness, the residue was neutralised to pH 8 with sodium hydroxide solution and purified on reverse phase silica eluting with a gradient of 30–40% methanol/ammonium carbonate buffer (2 g/l, pH 7) to give 2-(piperazin-4-yl)ethyl-N-[(5S)-3,9,10,11-tetramethoxy-6-7-dihydro-5H-dibenzo[a,c]cyclohepten-5-yl]carbamate.

Yield: 60%; $^1$H NMR (DMSO-d): 1.39 (s, 9H); 1.81–1.94
(m, 1H); 1.95–2.07 (m, 1H); 2.09–2.27 (m, 1H); 2.34 (m,
4H); 2.52–2.64 (m, 1H); 3.28 (m, 2H); 3.36 (s, 3H); 3.46 (s,
3H); 3.77 (s, 3H); 3.82 (s, 3H); 3.94–4.09 (m, 2H);
4.20–4.30 (m, 1H); 6.77 (s, 1H); 6.87 (dd, 1H); 6.92 (d, 1H);
7.25 (d, 1H); 7.86 (d, 1H).

EXAMPLE 8

N-[(5S)-3,9,10,11-Tetramethoxy-6-7-dihydro-5H-
dibenzo[a,c]cyclohepten-5-yl]-4-(1-methylpiperazin-
4-yl)-4-oxobutan-1-amide

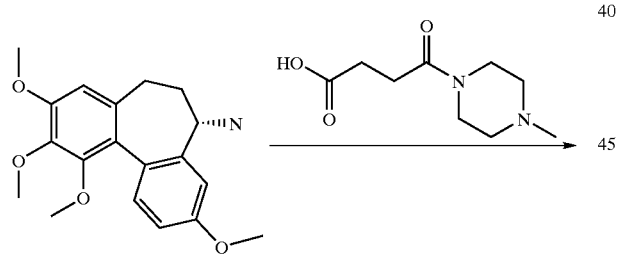

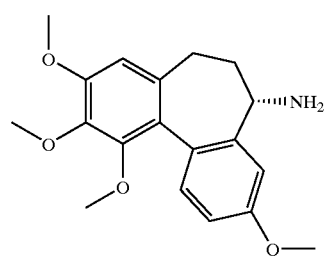

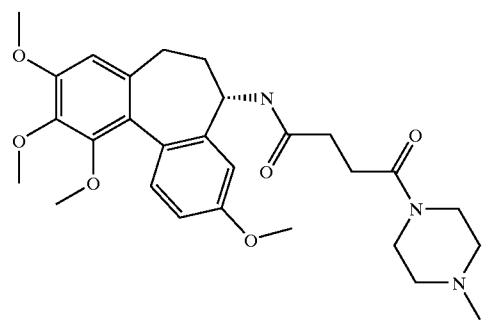

A solution of 4-(1-methylpiperazin-4-yl)-4-oxo butanoic acid (0.356 g; 1.78 mmol), EDCI (0.367 g; 1.78 mmol) and DMAP (0.05 g; 0.41 mmol) in dichloromethane (30 ml) was stirred for 35 minutes under argon atmosphere. (5S)-3,9,10,11-Tetramethoxy-6,7-dihydro-5H-dibenzo[a,c]cyclohepten-5-ylamine 0.45 g; 1.37 mmol) was then added and the mixture stirred at ambient temperature overnight. After evaporation of the solvent, the residue was purified by flash chromatography, eluting with dichloromethane/ethanol (95/5) to give after evaporation and trituration in pentane, the title compound as a white solid.

Yield: 60%; $^1$H NMR (DMSO-d$_6$): 1.85–1.96 (m, 1H);
2.01–2.15 (m, 1H); 2.16 (s, 3H); 2.22 (t, 2H); 2.26 (t, 2H);
2.33–2.42 (m, 1H); 2.47–2.53 (m, 1H); 3.35–3.46 (m, 4H);
3.46 (s, 3H); 3,79 (s, 3H); 3.82 (s, 3H); 3.84 (s, 3H);
4.44–4.56 (m, 1H), 6.79 (s, 1H); 6.86 (dd, 1H); 6.98 (d, 1H);
7.25 (d, 1H); 8.40 (d, 1H). MS-ESI: 512 [MH]$^+$.

| Elemental analysis | Found | C 65.51 | H 7.40 | N 8.19 |
|---|---|---|---|---|
| $C_{28}H_{37}N_3O_6$ | Requires | C 65.73 | H 7.29 | N 8.21 |

EXAMPLE 9

3-(1-Acetylpiperazin4-yl)propyl-N-[(5S)-3,9,10,11-
tetramethoxy-6-7-dihydro-5H-dibenzo[a,c]
cyclohepten-5-yl]carbamate

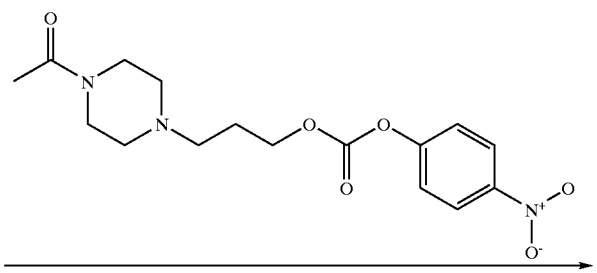

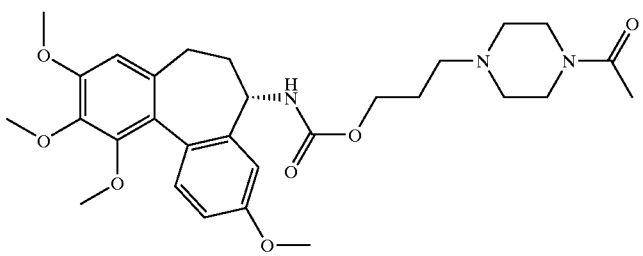

A solution of (5S)-3,9,10,11-tetramethoxy-6,7-dihydro-5H-dibenzo[a,c]cyclohepten-5-ylamine (0.329 g; 1 mmol) and 3-(4-acetylpiperazino)propyl 4-nitrophenylcarbonate (0.456 g; 1.3 mmol) in acetonitrile (8 ml) was heated under argon atmosphere at 70° C. for 6 hours. After evaporation to dryness, the residue was purified by flash chromatography eluting with dichloromethane/ethanol (93/7) to give the title compound.

Yield: 80%; $^1$H NMR (DMSO-$d_6$): 1.62–2.51 (m, 12H); 1.97 (s, 3H); 3.32–3.44 (m, 4H); 3.46 (s, 3H); 3.77 (s, 3H); 3.78 (s, 3H); 3.82 (s, 3H); 3.87–4.01 (m, 2H); 4.19–4.31 (m, 1H); 6.77 (s, 1H); 6.88 (dd, 1H); 6.92 (d, 1H); 7.25 (d, 1H); 7.80 (d, 1H). MS-ESI: 542 [MH]$^+$.

| Elemental analysis | Found | C 63.48 | H 7.25 | N 7.72 |
| --- | --- | --- | --- | --- |
| $C_{29}H_{39}N_3O_7$, 0.4 $H_2O$ | Requires | C 63.46 | H 7.31 | N 7.66 |

The starting material was prepared as follows:

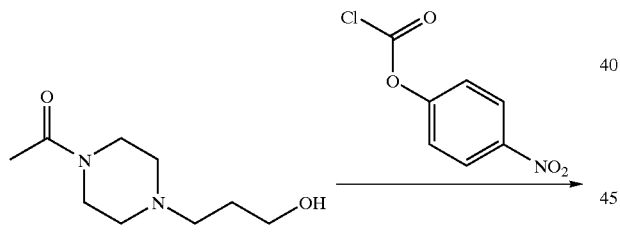

4-Nitrophenyl chloroformate (0.733 g; 3.63 mmol) was added to a solution of 3-(4-acetylpiperazin-1-yl)propanol [Synthesis (1997), 6, 643–648] (0.645 g; 3.46 mmol) and triethylamine (0.51 ml; 3.36 mmol) in dichloromethane (7 ml) under argon atmosphere at 0° C. The mixture was stirred at ambient temperature for 1 hour, evaporated to dryness and purified by flash chromatography, eluting with dichloromethane/ethanol (95/5) to give 3(-4-acetylpiperazino)propyl 4-nitrophenyl carbonate.

$^1$H NMR (CDCl$_3$): 1.96 (m, 2H); 2.09 (s, 3H); 2.39–2.48 (m, 4H); 2.51 (t, 2H); 3.47 (t, 3H); 3.63 (t, 2H); 3.68–3.78 (m, 2H); 4.38 (t, 2H); 7.39 (d, 2H); 8.29 (d, 2H).

EXAMPLE 10

4-Morpholino-4-oxobutyl-N-[(5S)-3,9,10,11-tetramethoxy-6,7-dihydro-5H-dibenzo[a-c]cyclohepten-5-yl]carbamate

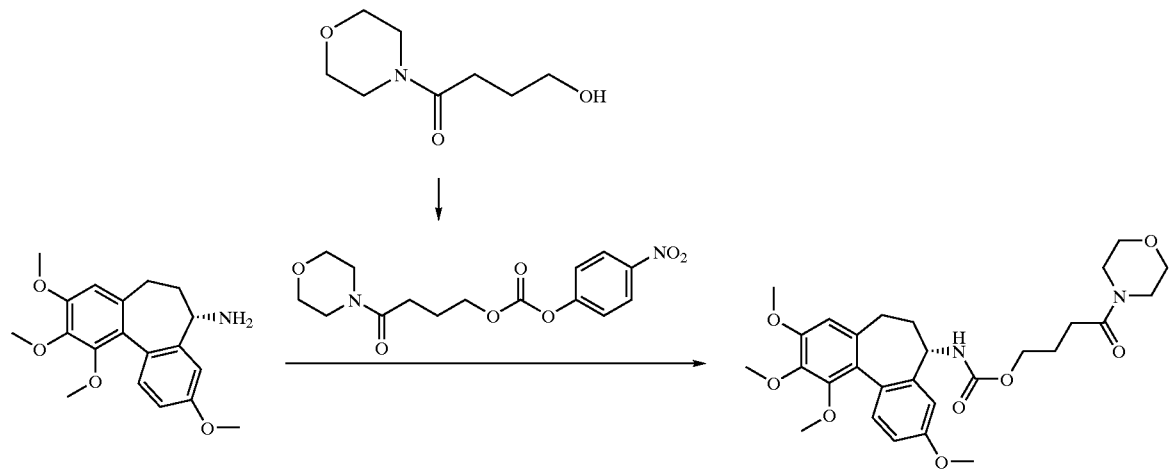

The compound was prepared using a similar method to that of Example 9, but replacing 3-(4-acetylpiperazino) propyl 4-nitrophenyl carbonate by 4-morpholino-4-oxobutyl 4-nitrophenylcarbonate.

Yield: 55%. $^1$H NMR (DMSO-d$_6$): 1.71–1.81 (m, 2H); 1.82–1.94 (m, 1H); 1.95–2.07 (s, 1H); 2.11–2.24 (s, 1H); 2.34 (t, 2H); 2.46 (m, 1H); 3.31–3.44 (m, 4H); 3.45 (s, 3H); 3.52 (m, 4H); 3.77 (s, 3H); 3.78 (s, 3H); 3.82 (s, 3H); 3.86–3.98 (m, 2H); 4.20–4.32 (m, 1H); 6.77 (s, 1H); 6.88 (dd, 1H); 6.92 (d, 1H); 7.25 (d, 1H); 7.80 (d, 1H). MS-ESI: 529 [MH]$^+$.

| Elemental analysis | Found | C 62.81 | H 6.95 | N 5.27 |
| --- | --- | --- | --- | --- |
| $C_{28}H_{36}N_2O_8$, 0.3 H$_2$O | Requires | C 62.98 | H 6.91 | N 5.25 |

The starting material was prepared using a similar method to that of example 9, starting from 4-morpholino4-oxobutyl 4-nitrophenyl carbonate.

Yield: 92%; $^1$H NMR (CDCl$_3$): 2.15 (m, 2H); 2.50 (t, 2H); 3.46–3.53 (m, 2H); 3.51–3.75 (m, 6H); 3.38 (t, 2H); 7.33 (d, 2H); 8.29 (d, 2H).

EXAMPLE 11

4-(1-Methylpiperazin-4-yl)-4-oxobutyl-N-[(5S)-3,9,10,11-tetramethoxy-6,7-dihydro-5H-dibenzo[a,c] cylcohepten-5-yl]carbamate

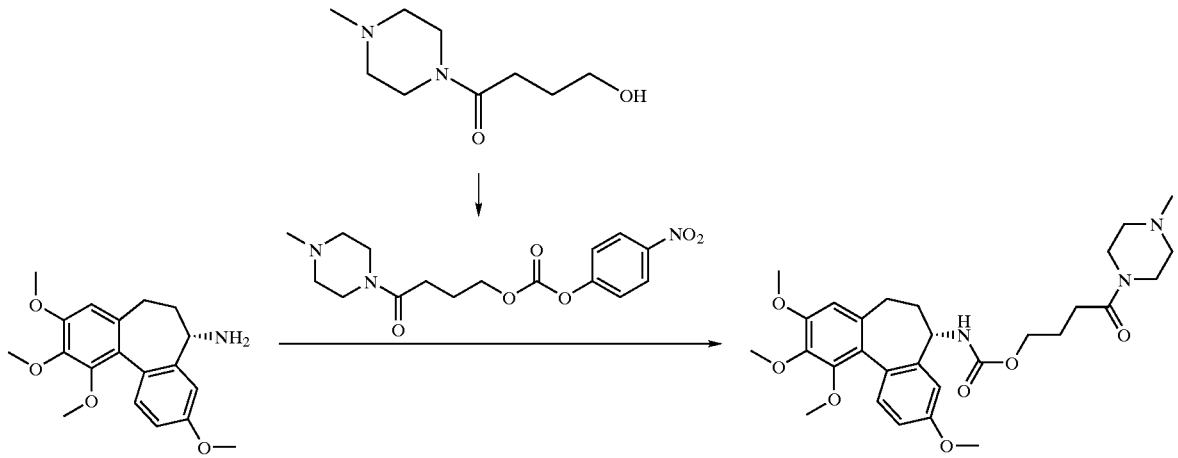

The title compound was prepared using a similar method to that of Example 9, but replacing 3-(4-acetylpiperazino) propyl 4-nitrophenyl carbonate by 4-methylpiperazin-1-yl) 4-oxobutyl 4-nitrophenyl carbonate.

Yield: 65%; $^1$H NMR (DMSO-d$_6$): 1.75 (m, 2H); 1.81–2.07 (m, 2H); 2.08–2.40 (m, 7H); 2.15 (s, 3H); 2.50–2.60 (m, 1H); 3.22–3.56 (m, 4H); 3.45 (s, 3H); 3.77 (s, 3H); 3.78 (s, 3H); 3.82 (s, 3H); 3.82–3.99 (m, 2H); 4.12–4.32 (m, 1H); 6.76 (s, 1H); 6.87 (dd, 1H); 6.92 (d, 1H); 7.25 (d, 1H); 7.80 (d, 1H). MS-ESI: 542 [MH]$^+$.

| Elemental analysis | Found | C 63.38 | H 7.58 | N 7.64 |
| --- | --- | --- | --- | --- |
| $C_{29}H_{39}N_3O_7$, 0.4 H$_2$O | Requires | C 63.46 | H 7.31 | N 7.66 |

The starting material was prepared using a similar method to that of Example 9, from 4-(4-methylpiperazin-1-yl)4-oxobutanol.

Yield: 65%. $^1$H NMR (CDCl$_3$): 2.08–2.19 (m, 2H); 2.32 (s, 3H); 2.35–2.46 (m, 4H); 2.49 (t, 2H); 3.51 (t, 2H); 2.66 (t, 2H); 4.38 (t, 2H); 7.39 (d, 2H); 8.29 (d, 2H).

What is claimed is:

1. A compound of the formula (I):

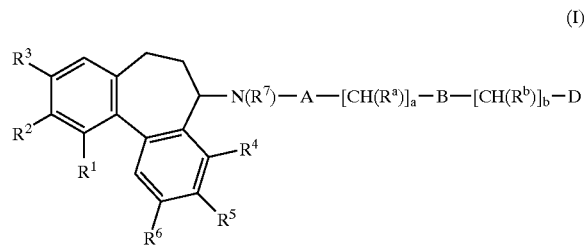

wherein:

R$^1$, R$^2$ and R$^3$ are each independently hydroxy, phosphoryloxy (—OPO$_3$H$_2$), C$_{1-4}$alkoxy or an in vivo hydrolysable ester of hydroxy, with the proviso that at least 2 of R$^1$, R$^2$ and R$^3$ are C$_{1-4}$alkoxy;

A is —CO—, —C(O)O—, —CON(R$^8$)—, —SO$_2$— or —SO$_2$N(R$^8$)— (wherein R$^8$ is hydrogen, C$_{1-4}$alkyl, C$_{1-3}$alkoxyC$_{1-3}$alkyl, aminoC$_{1-3}$alkyl or hydroxyC$_{1-3}$alkyl);

a is an integer from 1 to 4 inclusive;

R$^a$ and R$^b$ are independently selected from hydrogen, hydroxy and amino;

B is —O—, —CO—, —N(R$^9$)CO—, —CON(R$^9$)—, —C(O)O—, —N(R$^9$)—, —N(R$^9$)C(O)O—, —N(R$^9$)CON(R$^{10}$)—, —N(R$^9$)SO$_2$—, —SO$_2$N(R$^9$)— or a direct single bond (wherein R$^9$ and R$^{10}$ are independently selected from hydrogen, C$_{1-4}$alkyl, C$_{1-3}$alkoxyC$_{1-3}$alkyl, aminoC$_{1-3}$alkyl and hydroxyC$_{1-3}$alkyl);

b is 0 or an integer from 1 to 4 inclusive, (provided that when b is 0, B is a single direct bond);

D is carboxy, sulpho, tetrazolyl, imidazolyl, phosphoryloxy, hydroxy, amino, N—(C$_{1-4}$alkyl)amino, N,N-di(C$_{1-3}$alkyl)amino or of the formula —Y$^1$—(CH$_2$)$_c$R$^{11}$ or —NHCH(R$^{12}$)COOH; [wherein Y$^1$ is a direct single bond, —O—, —C(O)—, —N(R$^{13}$)—, —N(R$^{13}$)C(O)— or —C(O)N(R$^{13}$)— (wherein R$^{13}$ is hydrogen, C$_{1-4}$alkyl, C$_{1-3}$alkoxyC$_{2-3}$alkyl, aminoC$_{2-3}$alkyl or hydroxyC$_{2-3}$alkyl); c is 0 or an integer from 1 to 4 inclusive; R$^{11}$ is a 5–6-membered saturated heterocyclic group (linked via carbon or nitrogen) containing 1 or 2 ring heteroatoms, selected independently from O, S and N, or a 5–6-membered unsaturated or partially unsaturated heteroaryl group (linked via carbon or nitrogen) containing 1 or 2 ring heteroatoms, selected independently from O, S and N, which heterocyclic group or heteroaryl group may bear 1 or 2 substituents selected from:

oxo, hydroxy, halogeno, $C_{1-4}$alkyl, $C_{2-4}$alkanoyl, carbamoyl, $\underline{N}$—($C_{1-14}$alkyl)carbamoyl, $\underline{N},\underline{N}$-di-($C_{1-4}$alkyl)carbamoyl, hydroxy$C_{1-4}$alkyl, $C_{1-4}$alkoxy, cyano$C_{1-3}$alkyl, carbamoyl$C_{1-3}$alkyl, carboxy$C_{1-4}$alkyl, amino$C_{1-4}$alkyl, $\underline{N}$—$C_{1-4}$alkylamino$C_{1-4}$alkyl, di-$\underline{N},\underline{N}$—($C_{1-4}$alkyl)amino$C_{1-14}$alkyl, $C_{1-4}$alkoxy$C_{1-4}$alkyl, $C_{1-4}$alkylsulphonyl$C_{1-4}$alkyl and $R^{14}$ (wherein $R^{14}$ is a 5–6-membered saturated heterocyclic group (linked via carbon or nitrogen) containing 1 or 2 ring heteroatoms, selected independently from O, S and N, which heterocyclic group is optionally substituted by 1 or 2 substituents selected from:

oxo, hydroxy, halogeno, $C_{1-4}$alkyl, hydroxy$C_{1-4}$alkyl, $C_{1-4}$alkoxy, $C_{1-4}$alkoxy$C_{1-4}$alkyl and $C_{1-4}$alkylsulphonyl$C_{1-4}$alkyl);

$R^{12}$ is an amino acid side chain;

$R^5$ is $C_{1-4}$alkoxy;

$R^4$ and $R^6$ are each independently selected from: hydrogen, fluoro, nitro, amino, N—$C_{1-4}$alkylamino, N,N-di-($C_{1-4}$alkyl)amino, hydroxy, $C_{1-4}$alkoxy and $C_{1-4}$alkyl;

$R^7$ is hydrogen, $C_{1-4}$alkyl, $C_{1-3}$alkoxy$C_{1-3}$alkyl, amino $C_{1-3}$alkyl or hydroxy$C_{1-3}$alkyl;

or a pharmaceutically acceptable salt, solvate or pro-drug thereof.

2. A compound according to claim 1 where $R^1$, $R^2$ and $R^3$ are all methoxy
or a pharmaceutically acceptable salt, solvate or pro-drug thereof.

3. A compound according to claim 1 wherein:

$R^1$, $R^2$, and $R^3$ are all $C_{1-4}$alkoxy;

$R^4$ and $R^6$ are independently selected from hydrogen, hydroxy, $C_{1-3}$ alkoxy, and $C_{1-3}$alkyl;

$R^5$ is methoxy;

A is —CO—, —C(O)O— or —CONH—;

a is 1, 2 or 3;

B is —CO—, —NHCO—, —CONH, —C(O)O—, —NH—, —NHC(O)O—, NHCONH— or a single direct bond;

b is 0, 1 or 2;

D is carboxy, sulpho, phosphoryloxy, hydroxy, amino, $\underline{N}$—$C_{1-4}$ alkylamino, $\underline{N},\underline{N}$-di($C_{1-4}$alkyl)amino or of the formula —$Y^1(CH_2)_cR^{11}$ (wherein $Y^1$ is —NHC(O)— or —C(O)NH—; c is 1 or 2; $R^{11}$ is a 5–6-membered saturated heterocyclic group (linked via nitrogen) containing 1 or 2 ring heteroatoms, selected independently from O and N, which heterocyclic group may bear 1 or 2 substituents selected from:

$C_{1-4}$ alkyl, $C_{2-4}$alkanoyl, carbamoyl, cyano$C_{1-3}$alkyl, hydroxy$C_{1-3}$alkyl, carboxy$C_{1-3}$alkyl and amino$C_{1-3}$ alkyl);

$R^7$ is hydrogen;

or a pharmaceutically-acceptable salt, solvate or pro-drug thereof.

4. A compound according to claim 1 wherein:

$R^1$, $R^2$, and $R^3$ are all methoxy;

$R^4$ and $R^6$ are independently selected from hydrogen, hydroxy, methoxy and methyl;

$R^5$ is methoxy;

A is —CO—, —C(O)O— or —CONH—;

a is 2 or 3;

B is —CO—, —NHCO—, —CONH or a single direct bond;

b is 0 or 1;

D is carboxy, phosphoryloxy, hydroxy, amino, $\underline{N}$—$C_{1-4}$ alkylamino, $\underline{N},\underline{N}$-di($C_{1-4}$alkyl)amino or of the formula —$Y^1(CH_2)_cR^{11}$ (wherein $Y^1$ is —NHC(O)— or —C(O)NH—; c is 1 or 2; $R^{11}$ is piperazinyl, morpholinyl or piperidinyl, each of which is linked via a ring nitrogen atom and each ring is optionally substituted by 1 or 2 substituents selected from:

$C_{1-14}$alkyl, $C_{2-4}$alkanoyl, carbamoyl, cyano$C_{1-3}$alkyl, hydroxy$C_{1-3}$alkyl, carboxy$C_{1-3}$alkyl and amino$C_{1-3}$ alkyl);

$R^7$ is hydrogen;

or a pharmaceutically-acceptable salt, solvate or pro-drug thereof.

5. A compound of formula (II):

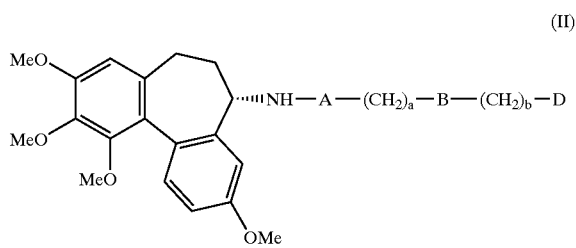

(II)

wherein a, b, A, B and D are as defined in claim 1;

or a pharmaceutically acceptable salt, solvate or prodrug thereof.

6. A compound according to claim 5 wherein:

A is —CO—, —C(O)O— or —CONH—;

a is 2 or 3;

B is —CO—, —NHCO—, —CONH or a single direct bond;

b is 0 or 1;

D is carboxy, phosphoryloxy, hydroxy, amino, $\underline{N}$—$C_{1-4}$ alkylamino, $\underline{N},\underline{N}$-di($C_{1-4}$alkyl)amino or of the formula —$Y^1(CH_2)_cR^{11}$ (wherein $Y^1$ is —NHC(O)— or —C(O)NH—; c is 1 or 2; $R^{11}$ is piperazinyl, morpholinyl or piperidinyl, each of which is linked via a ring nitrogen atom and each ring is optionally substituted by 1 or 2 substituents selected from:

$C_{1-4}$alkyl, $C_{2-4}$alkanoyl, carbamoyl, cyano$C_{1-3}$alkyl, hydroxy$C_{1-3}$alkyl, carboxy$C_{1-3}$alkyl and amino$C_{1-3}$ alkyl);

or a pharmaceutically acceptable salt, solvate or prodrug thereof.

7. A compound of formula (III):

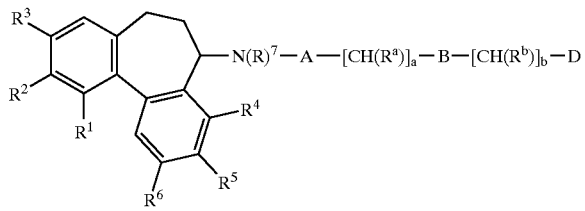

(III)

wherein:
$R^1$, $R^2$ and $R^3$ are each independently hydroxy, phosphoryloxy (—OPO$_3$H$_2$), $C_{1-4}$alkoxy or an in vivo hydrolysable ester of hydroxy, with the proviso that at least 2 of $R^1$, $R^2$ and $R^3$ are $C_{1-4}$alkoxy;
A is —CO—, —C(O)O—, —CON($R^8$)—, —SO$_2$— or —SO$_2$N($R^8$)— (wherein $R^8$ is hydrogen, $C_{1-4}$alkyl, $C_{1-3}$alkoxyC$_{2-3}$alkyl, aminoC$_{2-3}$alkyl or hydroxyC$_{2-3}$alkyl);
a is an integer from 1 to 4 inclusive;
$R^a$ and $R^b$ are independently selected from hydrogen, hydroxy and amino;
B is —O—, —CO—, —N($R^9$)CO—, —CON($R^9$)—, —C(O)O—, —N($R^9$)—, —N($R^9$)C(O)O—, —N($R^9$)CON($R^{10}$)—, —N($R^9$)SO$_2$—, —SO$_2$N($R^9$)— or a direct single bond (wherein $R^9$ and $R^{10}$ are independently selected from hydrogen, $C_{1-4}$alkyl, $C_{1-3}$alkoxyC$_{2-3}$alkyl, aminoC$_{2-3}$alkyl and hydroxyC$_{2-3}$alkyl);
b is 0 or an integer from 1 to 4 inclusive;
D is a 5–6-membered saturated heterocyclic group (linked via carbon or nitrogen) containing 1 or 2 ring heteroatoms, selected independently from O and N, which heterocyclic group may bear 1 or 2 substituents selected from:
oxo, hydroxy, halogeno, $C_{1-4}$alkyl, $C_{2-4}$alkanoyl, carbamoyl, N—($C_{1-4}$alkyl)carbamoyl, N,N-di-($C_{1-4}$alkyl)carbamoyl, hydroxyC$_{1-4}$alkyl, $C_{1-4}$alkoxy, cyanoC$_{1-3}$alkyl, carbamoylC$_{1-3}$alkyl, carboxyC$_{1-4}$alkyl, aminoC$_{1-4}$alkyl, N—$C_{1-4}$alkylaminoC$_{1-4}$alkyl, di-N,N—($C_{1-4}$alkyl)aminoC$_{1-4}$alkyl, $C_{1-4}$alkoxyC$_{1-4}$alkyl, $C_{1-4}$alkylsulphonylC$_{1-4}$alkyl and $R^{14}$ (wherein $R^{14}$ is a 5–6-membered saturated heterocyclic group (linked via carbon or nitrogen) containing 1 or 2 ring heteroatoms, selected independently from O and N, which heterocyclic group is optionally substituted by 1 or 2 substituents selected from:
oxo, hydroxy, halogeno, $C_{1-4}$alkyl, hydroxyC$_{1-4}$alkyl, $C_{1-4}$alkoxy, $C_{1-4}$alkoxyC$_{1-4}$alkyl and $C_{1-4}$alkylsulphonylC$_{1-4}$alkyl);
$R^5$ is $C_{1-4}$alkoxy;
$R^4$ and $R^6$ are each independently selected from:
hydrogen, halogeno, nitro, amino, N—$C_{1-4}$alkylamino, N,N-di-($C_{1-4}$alkyl)amino, hydroxy, $C_{1-4}$alkoxy and $C_{1-4}$alkyl;
$R^7$ is hydrogen, $C_{1-4}$alkyl, $C_{1-3}$alkoxyC$_{1-3}$alkyl, amino $C_{1-3}$alkyl or hydroxyC$_{1-3}$alkyl;
or a pharmaceutically acceptable salt, solvate or pro-drug thereof.

8. A compound according to claim 7 wherein:
$R^1$, $R^2$, and $R^3$ are all $C_{1-4}$alkoxy;
$R^4$ and $R^6$ are independently selected from hydrogen, hydroxy, $C_{1-3}$ alkoxy, and $C_{1-3}$alkyl;

$R^5$ is methoxy;
A is —CO—, —C(O)O— or —CONH—;
a is 1, 2 or 3;
B is —CO—, —NHCO—, —CONH, —C(O)O—, —NH—, —NHC(O)O—, NHCONH— or a single direct bond;
b is 0, 1 or 2;
D is piperazinyl or morpholinyl or piperidinyl, each ring being optionally substituted by 1 or 2 substituents selected from $C_{1-4}$alkyl, $C_{2-4}$alkanoyl, carbamoyl, cyanoC$_{1-3}$alkyl, hydroxyC$_{1-3}$alkyl, carboxyC$_{1-3}$alkyl and aminoC$_{1-3}$alkyl;
$R^7$ is hydrogen;
or a pharmaceutically-acceptable salt, solvate or pro-drug thereof.

9. A compound according to claim 7 wherein:
$R^1$, $R^2$, and $R^3$ are all methoxy;
$R^4$ and $R^6$ are independently selected from hydrogen, hydroxy, methoxy and methyl;
$R^5$ is methoxy;
A is —CO—, —C(O)O— or —CONH—;
a is 2 or 3;
B is —CO—, —NHCO—, —CONH or a single direct bond;
b is 0 or 1;
D is piperazino or morpholino, each ring being optionally substituted by 1 or 2 substituents selected from methyl, ethyl, acetyl, propionyl, carbamoyl and 2-hydroxyethyl;
$R^7$ is hydrogen;
or a pharmaceutically-acceptable salt, solvate or pro-drug thereof.

10. A compound according to claim 7 wherein:

(IV)

MeO—[structure]—NH—A—(CH$_2$)$_a$—B—(CH$_2$)$_b$—D
MeO
MeO
OMe wherein a, b, A, B and D are as hereinabove defined in claim 7;
or a pharmaceutically-acceptable salt, solvate or pro-drug thereof.

11. A compound according to claim 10 wherein:
A is —CO—, —C(O)O— or —CONH—;
a is 2 or 3;
B is —CO—, —NHCO—, —CONH or a single direct bond;
b is 0 or 1;
D is piperazino or morpholino, each ring being optionally substituted by 1 or 2 substituents selected from methyl, ethyl, acetyl, propionyl, carbamoyl and 2-hydroxyethyl;
or a pharmaceutically acceptable salt, solvate or pro-drug thereof.

12. A compound according to claim 10 wherein:

A is —CO—, —C(O)O— or —CONH—;

a is 2 or 3;

B is —CO—, —NHCO—, —CONH or a single direct bond;

b is 0 or 1;

D is morpholino, 4-methylpiperazin-1-yl or 4-acetylpiperazin-1-yl;

or a pharmaceutically acceptable salt, solvate or pro-drug thereof.

13. A compound selected from:

N-[(5S)-3,9,10,11-tetramethoxy-6,7-dihydro-5H-dibenzo[a,c]cyclohepten-5-yl]-2-[2-aminoacetylamino]acetamide;

4-oxo4-[(5S)-3,9,10,1 1-tetramethoxy-6,7-dihydro-5H-dibenzo[a,c]cyclohepten-5-yl]amino]butyl disodium phosphate;

N-{N-[2-(imidazol-1-yl)ethyl]carbamoyl}-5(S)-3,9,10,11-tetramethoxy-6,7-dihydro-5H-dibenzo[a,c]cyclohepten-5-ylamine; and 2-{N-[(5S)-3,9,10,11-tetramethoxy-6,7-dihydro-5H-dibenzo[a,c]cyclohepten-5-yl]carbamoyloxy}ethyl disodium phosphate;

2-morpholinoethyl N-[(5S)-3,9,10,11-tetramethoxy-6,7-dihydro-5H-dibenzo[a,c]cyclohepten-5-yl]carbamate;

3-(1-methylpiperazin-4-yl)propyl N-[(5S)-3,9,10,11-tetramethoxy-6,7-dihydro-5H-dibenzo[a,c]cyclohepten-5-yl]carbamate;

N-[(5S)-3,9,10,11-tetramethoxy-6,7-dihydro-5H-dibenzo[a,c]cyclohepten-5-yl]-2-[2-aminoacetylamino]acetamide;

2-(1-acetylpiperazin-4-yl)ethyl-N-[(5S)-3,9,10,11-tetramethoxy-6-7-dihydro-5H-dibenzo[a,c]cyclohepten-5-yl]carbamate;

N-[(5S)-3,9,10,11-tetramethoxy-6-7-dihydro-5H-dibenzo[a,c]cyclohepten-5-yl]-4-(1-methylpiperazin-4-yl)-4-oxobutan-1-amide;

4-oxo-4-[(5S)-3,9,10,11-tetramethoxy-6,7-dihydro-5H-dibenzo[a,c]cyclohepten-5-yl]amino]butyl disodium phosphate;

N-{N-[2-(imidazol-1-yl)ethyl]carbamoyl}-5(S)-3,9,10,11-tetramethoxy-6,7-dihydro-5H-dibenzo[a,c]cyclohepten-5-ylamine;

3-(1-acetylpiperazin4-yl) propyl-N-[(5S)-3,9,10,11-tetramethoxy-6-7dihydro-5H-dibenzo[a,c]cyclohepten-5-yl]carbamate;

N-1-[(5S)-3,9,10,11-tetramethoxy-6,7-dihydro-5H-dibenzo[a,c]cyclohepten-5-yl]carbamoyloxy]ethyl disodiumphosphate;

4-morpholino-4-oxobutyl-N-[(5S)-3,9,10,11-tetramethoxy-6,7-dihydro-5H-dibenzo[a-c]cyclohepten-5-yl]carbamate; and 4-(1-methylpiperazin-4-yl)-4-oxobutyl-N-[(5S)-3,9,10,11-tetramethoxy-6,7-dihydro-5H-dibenzo[a,c]cylohepten-5-yl]carbamate;

and pharmaceutically-acceptable salts, solvates or pro-drugs thereof.

14. A pharmaceutical composition comprising a compound according to any one of claims 1 to 13 or a pharmaceutically acceptable salt, solvate or pro-drug thereof, in association with a pharmaceutically acceptable carrier.

15. A method for the production of a vascular damaging effect in a warm-blooded animal in need thereof, comprising administering to said animal a compound according to any one of claims 1 to 13 or a pharmaceutically-acceptable salt, solvate or pro-drug thereof.

16. A method for the production of a vascular damaging effect in a warm-blooded animal in need thereof, comprising administering to said animal, in divided doses, a compound according to any one of claims 1 to 13 or a pharmaceutically-acceptable salt, solvate or prodrug thereof.

\* \* \* \* \*